United States Patent
Masaki et al.

(10) Patent No.: US 9,950,989 B2
(45) Date of Patent: Apr. 24, 2018

(54) CYCLIC HYDROCARBON COMPOUND

(71) Applicant: TOA EIYO LTD., Chuo-ku (JP)

(72) Inventors: Hidekazu Masaki, Saitama (JP);
Masayuki Kageyama, Saitama (JP)

(73) Assignee: TOA EIYO LTD., Chuo-ku (JP)

( * ) Notice: Subject to any disclaimer, the term of this patent is extended or adjusted under 35 U.S.C. 154(b) by 0 days.

(21) Appl. No.: 15/118,696

(22) PCT Filed: Feb. 13, 2015

(86) PCT No.: PCT/JP2015/053979
§ 371 (c)(1),
(2) Date: Aug. 12, 2016

(87) PCT Pub. No.: WO2015/122494
PCT Pub. Date: Aug. 20, 2015

(65) Prior Publication Data
US 2017/0050919 A1    Feb. 23, 2017

(30) Foreign Application Priority Data

Feb. 14, 2014  (JP) ................................ 2014-026617

(51) Int. Cl.

| | |
|---|---|
| C07C 247/14 | (2006.01) |
| C07D 207/335 | (2006.01) |
| C07D 277/28 | (2006.01) |
| C07D 307/52 | (2006.01) |
| A61K 31/13 | (2006.01) |
| C07C 223/04 | (2006.01) |
| C07C 271/24 | (2006.01) |
| C07D 333/20 | (2006.01) |
| C07D 333/22 | (2006.01) |
| C07D 333/32 | (2006.01) |
| C07C 233/41 | (2006.01) |
| C07C 233/79 | (2006.01) |

(52) U.S. Cl.
CPC .......... *C07C 223/04* (2013.01); *C07C 233/41* (2013.01); *C07C 233/79* (2013.01); *C07C 247/14* (2013.01); *C07C 271/24* (2013.01); *C07D 207/335* (2013.01); *C07D 277/28* (2013.01); *C07D 307/52* (2013.01); *C07D 333/20* (2013.01); *C07D 333/22* (2013.01); *C07D 333/32* (2013.01)

(58) Field of Classification Search
None
See application file for complete search history.

(56) References Cited

U.S. PATENT DOCUMENTS

| 5,571,796 A * | 11/1996 | Srivastava ............. C07H 15/18 514/42 |
|---|---|---|
| 5,866,601 A | 2/1999 | Lew et al. |
| 5,952,375 A | 9/1999 | Bischofberger et al. |
| 6,225,341 B1 | 5/2001 | Bischofberger et al. |
| 2005/0176758 A1 | 8/2005 | Bischofberger et al. |
| 2014/0051756 A1 | 2/2014 | Sugiyama |

FOREIGN PATENT DOCUMENTS

| CN | 1756740 A | 4/2006 |
|---|---|---|
| JP | 11-501908 A | 2/1999 |
| JP | 2012-236814 A | 12/2012 |
| WO | 2012/147902 A1 | 11/2012 |

OTHER PUBLICATIONS

Hayashida, M. et al. Novel synthesis of penta-N,O-acetylvaliolamine. Journal of Carbohydrate Chemistry. 1998, vol. 7, p. 83.*

(Continued)

*Primary Examiner* — Zinna Northington Davis
(74) *Attorney, Agent, or Firm* — Oblon, McClelland, Maier & Neustadt, L.L.P.

(57) ABSTRACT

Provided is a novel compound having an excellent suppression effect against arrhythmia including atrial fibrillation and being useful as a pharmaceutical product without antiviral effect. Disclosed is a compound represented by the following General Formula (I), a pharmaceutically acceptable salt thereof, or a solvate thereof (in the formula, the dotted line portion represents a single bond or a double bond; $R^1$ represents an optionally substituted $C_{1-6}$ alkyl group; Q represents an oxygen atom, a sulfur atom, or $NR^5$; $R^2$ represents —(C=O)—$R^6$, —CHR$^6$R$^7$, or —CH$_2$OR$^8$; and $R^3$ and $R^4$, which may be identical or different, each represent an amino group, an azide group, or —X—$R^9$, with the proviso that any one of $R^3$ and $R^4$ is an amino group).

(I)

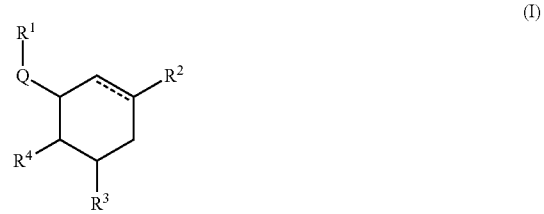

8 Claims, No Drawings

(56) References Cited

OTHER PUBLICATIONS

J. Reisinger, et al., "Prospective Comparison of Flecainide Versus Sotalol for Immediate Cardioversion of Atrial Fibrillation," The American Journal of Cardiology, Jun. 15, 1998, vol. 81, pp. 1450-1454.
T. Machida, et al., "Effects of a Highly Selective Acetylcholine-Activated K+Channel Blocker on Experimental Atrial Fibrillation," Circulation: Arrhthmia and Electrophysiology, 2011, vol. 4, pp. 94-102.
A. Takahara, et al., "Electrophysiological Effects of an Anti-influenza Drug Oseltamivir on the Guinea-Pig Atrium: Comparison with Those of Pilsicainide," Biological and Pharmaceutical Bulletin, Oct. 2013, vol. 36, No. 10, pp. 1650-1652.
International Search Report dated May 12, 2015 in PCT/JP2015/053979 Filed Feb. 13, 2015.
Office Action dated May 10, 2017 in Chinese Patent Application No. 201580008469.2 (with English translation of category of cited documents).

\* cited by examiner

CYCLIC HYDROCARBON COMPOUND

FIELD OF THE INVENTION

The present invention relates to a cyclic hydrocarbon compound useful as a therapeutic agent for arrhythmia and a pharmaceutical agent containing the same.

BACKGROUND OF THE INVENTION

Atrial fibrillation is arrhythmia in which the atrium is excited at a frequency of 300 to 500 times per minute and this excitation wave is transmitted to the atrioventricular node so that the ventricular activation becomes irregular. The morbidity rate of atrial fibrillation in Japan is estimated to approximately 0.5 to 1% of total population. In recent years, in accordance with an increase in elderly population and an increase in the number of patients having lifestyle-related diseases, particularly, hypertension in Japan and other countries, the morbidity rate of atrial fibrillation tends to increase. Since atrial fibrillation has the risk of being associated with cardiogenic brain embolism in addition to the risk of causing heart failure accompanied by palpitations or reduced cardiac function, the need for treatment is very high.

In addition, atrial fibrillation is progressive arrhythmia, and atrial fibrillation symptoms are repeated so that the number of paroxysm is gradually increased and a period of time of occurrences is prolonged. Thus, atrial fibrillation gradually becomes chronic. Under the circumstances that the rate of chronicity of atrial fibrillation is as high as about 5 to 10% per year and there is a concern that the risk of heart failure or stroke is increased in association with the chronicity of atrial fibrillation, it is reported that a pharmaceutical effect of conventional antiarrhythmic drugs is reduced or become invalid (Non Patent Document 1). However, there is no antiarrhythmic drug capable of completely suppressing atrial fibrillation that becomes chronic, and a catheter ablation method, which is effective as a non-pharmacological therapy, also has problems of application or complications associated with procedure. Thus, it cannot be said that the catheter ablation method is a therapeutic method as the first-line choice. As described above, the effective therapeutic method against atrial fibrillation has not been established yet, and thus there is a demand for development of a therapeutic agent for atrial fibrillation that is safe and highly effective.

For the pharmacological treatment of atrial fibrillation, Na channel blockers (mainly, Class I drug in Vaughan Williams classification) or K channel blockers (mainly, Class III drug in Vaughan Williams classification) having a myocardial refractory period prolonging effect are used as an atrial fibrillation prevention or a drug for maintaining sinus rhythm. Since these conventional antiarrhythmic drugs act on ion channels of both of the atrial myocardium and the ventricular myocardium, not only the atrial refractory period prolonging effect but also side effects such as suppression of the left ventricular function due to a negative inotropic effect and an arrhythmogenic effect caused by a QT-prolonging effect exist. In recent years, with regard to development of the atrial fibrillation therapeutic agent, searching for drug development has been conducted in which ion channels, such as $IK_{ur}$ and $IK_{Ach}$, which are expressed or function specifically to the atrium, are used as a target, and pharmaceutical products that are intended to overcome the problems of conventional drugs have been developed (Non Patent Document 2).

In Patent Document 1, it is clearly described that oseltamivir, which is known as an anti-influenza drug, an active metabolite thereof, or a glucuronic acid conjugate thereof has an atrial fibrillation suppression effect against an atrial fibrillation model.

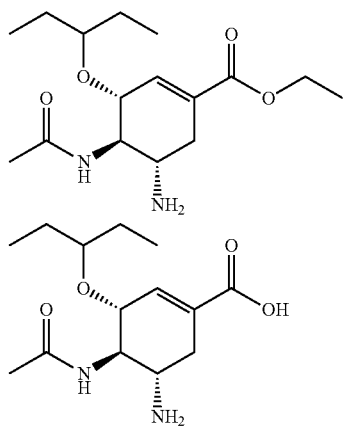

CITATION LIST

Patent Document

Patent Document 1: JP 2012-236814 A

Non Patent Documents

Non Patent Document 1: The American Journal of Cardiology, ELSEVIER, (German), 1998, Vol. 81, p. 1450-1454
Non Patent Document 2: Circulation: Arrhythmia and Electrophysiology, American Heart Association, (USA), 2011, Vol. 4, p. 94-102

SUMMARY OF THE INVENTION

Problems to be Solved by the Invention

However, regarding these compounds, there is also a concern that resistant viruses are expressed depending on the method of using these compounds, and thus it is desirable to separate the suppressive effect for atrial fibrillation and the antiviral activity. In addition, there is also a problem of stability in a living organism.

Therefore, an object of the present invention is to provide novel compounds having an excellent suppressive effect against arrhythmia including atrial fibrillation and being useful as a pharmaceutical product without antiviral effect.

Means for Solving the Problem

In this regard, the present inventors have synthesized various compounds and screened these compounds by utilizing the atrial effective refractory period of small animals as an indicator. Thus, the inventors found that compounds represented by the following General Formula (I) exhibit an excellent atrial effective refractory period prolonging effect, are useful as a prophylactic or therapeutic agent for arrhythmia diseases including atrial fibrillation, have a weak anti-neuraminidase activity that is an antiviral effect mechanism of oseltamivir, and also have satisfactory stability. Thus, the inventors have completed the present invention.

That is, the present invention is to provide the following [1] to [12].

[1] A compound represented by the following General Formula (I), a pharmaceutically acceptable salt thereof, or a solvate thereof:

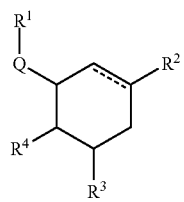

wherein the dotted line portion represents a single bond or a double bond;

$R^1$ represents an optionally substituted $C_{1-6}$ alkyl group;

Q represents an oxygen atom, a sulfur atom, or $NR^5$;

$R^5$ represents a hydrogen atom, an optionally substituted $C_{1-6}$ alkyl group, or an optionally substituted non-aromatic heterocyclic ring formed by combining with $R^1$ and an adjacent nitrogen atom;

$R^2$ represents —(C=O)—$R^6$, —CHR$^6$R$^7$, or —CH$_2$OR$^8$;

$R^6$ represents an optionally substituted $C_{1-6}$ alkyl group, an optionally substituted aryl group, or an optionally substituted heteroaryl group;

$R^7$ represents a hydroxyl group or an optionally substituted $C_{1-6}$ alkoxy group;

$R^8$ represents an optionally substituted $C_{1-6}$ alkyl group;

$R^3$ and $R^4$, which may be identical or different, each represent an amino group, an azide group, or —X—$R^9$;

$R^9$ represents a hydrogen atom, an optionally substituted $C_{1-6}$ alkyl group, —(C=O)—$R^{10}$, or —(C=O)—NR$^{11}$R$^{12}$;

$R^{10}$ represents an optionally substituted $C_{1-6}$ alkyl group, an optionally substituted $C_{1-6}$ alkoxy group, an optionally substituted aryl group, or an optionally substituted heteroaryl group;

$R^{11}$ and $R^{12}$, which may be identical or different, each represent a hydrogen atom or an optionally substituted $C_{1-6}$ alkyl group;

X represents an oxygen atom or $NR^{13}$; and $R^{13}$ represents a hydrogen atom, an optionally substituted $C_{1-6}$ alkyl group, or an optionally substituted non-aromatic heterocyclic ring formed by combining with $R^9$ and an adjacent nitrogen atom, with the proviso that any one of $R^3$ and $R^4$ is an amino group.

[2] The compound according to [1], a pharmaceutically acceptable salt thereof, or a solvate thereof, wherein in the above General Formula (I), the dotted line portion represents a double bond.

[3] A compound represented by General Formula (II), a pharmaceutically acceptable salt thereof, or a solvate thereof:

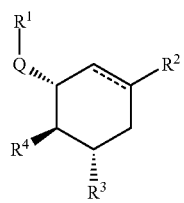

wherein each substituents are defined as above General Formula (I).

[4] The compound according to any one of [1] to [3], a pharmaceutically acceptable salt thereof, or a solvate thereof, wherein the substituent which the $C_{1-6}$ alkyl group, the aryl group, the heteroaryl group, the $C_{1-6}$ alkoxy group, or the non-aromatic heterocyclic ring has is one to five substituents selected from a halogen atom, a hydroxyl group, a cyano group, a nitro group, a $C_{1-6}$ alkyl group, a $C_{2-6}$ alkenyl group, a $C_{1-6}$ alkoxy group, an acyl group, a carboxyl group, a $C_{1-6}$ alkylcarbonylamino group, a $C_{1-6}$ alkoxycarbonyl group, a carbamoyl group, a sulfamoyl group, a $C_{1-6}$ alkylsulfanyl group, a $C_{1-6}$ alkylsulfenyl group, a $C_{1-6}$ alkylsulfonyl group, an amino group, a $C_{1-6}$ alkylamino group, a $C_{1-6}$ dialkylamino group, an aryl group, a heteroaryl group, and a non-aromatic heterocyclic ring group.

[5] The compound according to any one of [1] to [4], a pharmaceutically acceptable salt thereof, or a solvate thereof, wherein Q is an oxygen atom.

[6] The compound according to any one of [1] to [5], a pharmaceutically acceptable salt thereof, or a solvate thereof, wherein $R^3$ is an amino group and $R^4$ is —NH(C=O)—$R^{10}$ or —NH—(C=O)—NR$^{11}$R$^{12}$.

[7] A pharmaceutical agent containing the compound according to any one of [1] to [6], a pharmaceutically acceptable salt thereof, or a solvate thereof.

[8] The pharmaceutical agent according to [7], wherein the agent is a therapeutic agent for arrhythmia.

[9] A pharmaceutical agent composition comprising:
the compound according to any one of [1] to [6], a pharmaceutically acceptable salt thereof, or a solvate thereof; and
a pharmaceutically acceptable carrier.

[10] The compound according to any one of [1] to [6], a pharmaceutically acceptable salt thereof, or a solvate thereof, for use in the treatment of arrhythmia.

[11] Use of the compound according to any one of [1] to [6], a pharmaceutically acceptable salt thereof, or a solvate thereof, for the production of a therapeutic agent for arrhythmia.

[12] A method for treating arrhythmia, containing administering an effective amount of the compound according to any one of [1] to [6], a pharmaceutically acceptable thereof, or a solvate thereof to a patient in need thereof.

Advantageous Effects of the Invention

The compound of the present invention exhibits an excellent atrial effective refractory period prolonging effect, also has high safety, and is useful as a stopper for arrhythmia diseases including atrial fibrillation and a prophylactic or therapeutic agent therefor.

DETAILED DESCRIPTION OF THE INVENTION

A compound (I) of the present invention has a feature in that $R^2$ is an acyl group, a hydroxymethyl group, or an alkoxymethyl group.

In the present specification, examples of the "halogen atom" include a fluorine atom, a chlorine atom, a bromine atom, and an iodine atom. The "halogen atom" is preferably a fluorine atom or a chlorine atom.

In the present specification, "$C_{n1-n2}$" indicates that the number of carbon atoms included in the substituent is n1 to n2.

In the present specification, the "$C_{1-6}$ alkyl group" indicates a linear alkyl group having 1 to 6 carbon atoms, or a branched or cyclic alkyl group having 3 to 6 carbon atoms. Examples of the $C_{1-6}$ alkyl group include a methyl group, an ethyl group, an n-propyl group, an isopropyl group, a 1-ethylpropyl group, an n-butyl group, an isobutyl group, a sec-butyl group, a tert-butyl group, a 1-ethylbutyl group, an n-pentyl group, an n-hexyl group, a cyclopropyl group, a cyclobutyl group, a cyclopentyl group, and a cyclohexyl group. In General Formula (I), the "$C_{1-6}$ alkyl group" of the optionally substituted $C_{1-6}$ alkyl group represented by $R^1$ is preferably a $C_{4-6}$ alkyl group, more preferably a 1-ethylpropyl group or an n-pentyl group, and particularly preferably a 1-ethylpropyl group. The "$C_{1-6}$ alkyl group" of the optionally substituted $C_{1-6}$ alkyl group represented by $R^6$ is preferably a $C_{4-6}$ alkyl group and more preferably an n-butyl group, a tert-butyl group, an n-pentyl group, or a cyclohexyl group. The "$C_{1-6}$ alkyl group" of the optionally substituted $C_{1-6}$ alkyl group represented by $R^5$, $R^8$, $R^9$, $R^{11}$, $R^{12}$, or $R^{13}$ is preferably a $C_{1-4}$ alkyl group and more preferably a methyl group or an ethyl group. The "$C_{1-6}$ alkyl group" of the optionally substituted $C_{1-6}$ alkyl group represented by $R^{10}$ is preferably a $C_{1-4}$ alkyl group, more preferably a methyl group, an ethyl group, an n-propyl group, an isopropyl group, a sec-butyl group, or a tert-butyl group, and particularly preferably a methyl group, a sec-butyl group, or a tert-butyl group.

In the present specification, the "$C_{2-6}$ alkenyl group" indicates a linear alkenyl group having 2 to 6 carbon atoms, or a branched or cyclic alkenyl group having 3 to 6 carbon atoms. Examples of the $C_{2-6}$ alkenyl group include a vinyl group, a 1-propenyl group, a 2-propenyl group, an isopropenyl group, a 2-methyl-1-propenyl group, a 1-butenyl group, a 2-butenyl group, a 3-butenyl group, a 1-pentenyl group, a 2-pentenyl group, a 1-hexenyl group, a 2-hexenyl group, a 1-cyclohexenyl group, a 2-cyclohexenyl group, and a 3-cyclohexenyl group.

In the present specification, the "aryl group" indicates a monocyclic or polycyclic aromatic hydrocarbon group having 6 to 10 carbon atoms. Examples of the aryl group include a phenyl group, a 1-naphthyl group, and a 2-naphthyl group. In General Formula (I), the "aryl group" of the optionally substituted aryl group represented by $R^6$ or $R^{10}$ is preferably a phenyl group.

In the present specification, the "heteroaryl group" indicates a monocyclic or polycyclic aromatic heterocyclic group containing one to three of oxygen atoms, nitrogen atoms, or sulfur atoms, and the binding position is not particularly limited as long as it is chemically stable. Examples of the heteroaryl group include a pyrrolyl group, a furyl group, a thienyl group, a pyrazolyl group, an imidazolyl group, an oxazolyl group, an isoxazolyl group, a thiazolyl group, an isothiazolyl group, an oxadiazolyl group, a thiadiazolyl group, a triazolyl group, a pyridyl group, a pyridazinyl group, a pyrimidinyl group, a pyrazinyl group, a quinolyl group, an isoquinolyl group, a benzimidazolyl group, an indolyl group, a benzisoxazolyl group, a benzoxazolyl group, a benzisothiazolyl group, and a benzothiazolyl group. In General Formula (I), the "heteroaryl group" of the optionally substituted heteroaryl group represented by $R^6$ or $R^{10}$ is preferably a 5-membered to 6-membered monocyclic heteroaryl group, and more preferably a pyrrolyl group, a furyl group, a thienyl group, an oxazolyl group, or a thiazolyl group.

In the present specification, the "$C_{1-6}$ alkoxy group" indicates a group to which the "$C_{1-6}$ alkyl group" described above is bonded via one oxygen atom. Examples of the $C_{1-6}$ alkoxy group include a methoxy group, an ethoxy group, an n-propoxy group, an isopropoxy group, an n-butoxy group, a sec-butoxy group, an isobutoxy group, a tert-butoxy group, an n-pentoxy group, an n-hexoxy group, a cyclopropoxy group, a cyclobutoxy group, a cyclopentoxy group, and a cyclohexoxy group. In General Formula (I), the "$C_{1-6}$ alkoxy group" of the optionally substituted $C_{1-6}$ alkoxy group represented by $R^7$ or $R^{10}$ is preferably a $C_{1-4}$ alkoxy group and more preferably a methoxy group or an ethoxy group.

In the present specification, the "non-aromatic heterocyclic ring" indicates a 3-membered to 10-membered non-aromatic heterocyclic ring containing one or two or more nitrogen atoms and zero to one oxygen atom or sulfur atom. Examples of the non-aromatic heterocyclic ring include an azetidine ring, a pyrrolidine ring, a piperidine ring, a piperazine ring, a hexamethyleneimine ring, a heptamethyleneimine ring, a homopiperazine ring, a 2,5-diazabicyclo[2.2.1]heptane ring, a morpholine ring, and a thiomorpholine ring. In General Formula (I), the "non-aromatic heterocyclic ring" in a case where $R^5$ or $R^{13}$ is combined together with $R^1$ or $R^9$ and the adjacent nitrogen atom to form an optionally substituted non-aromatic heterocyclic ring is preferably an azetidine ring, a morpholine ring, or a pyrrolidine ring, and more preferably an azetidine ring or a pyrrolidine ring.

In the present specification, the expression "optionally substituted" means either "unsubstituted" or having one to five, and preferably one to three, identical or different substituents at substitutable positions. In the present specification, when the $C_{1-6}$ alkyl group, the aryl group, the heteroaryl group, the $C_{1-6}$ alkoxy group, or the non-aromatic heterocyclic ring optionally has a substituent, examples of the substituent include a halogen atom, a hydroxyl group, a cyano group, a nitro group, a $C_{1-6}$ alkyl group, a $C_{2-6}$ alkenyl group, a $C_{1-6}$ alkoxy group, an acyl group, a carboxyl group, a $C_{1-6}$ alkylcarbonylamino group, a $C_{1-6}$ alkoxycarbonyl group, a carbamoyl group, a sulfamoyl group, a $C_{1-6}$ alkylsulfanyl group, a $C_{1-6}$ alkylsulfenyl group, a $C_{1-6}$ alkylsulfonyl group, an amino group, a $C_{1-6}$ alkylamino group, a $C_{1-6}$ dialkylamino group, an aryl group, a heteroaryl group, and a non-aromatic heterocyclic ring group, and these are further optionally substituted.

The $C_{1-6}$ alkyl or $C_{1-6}$ alkoxy group which has a substituent is preferably a $C_{1-6}$ alkyl or $C_{1-6}$ alkoxy group which has one to five, and preferably one to three, substituents selected from halogen atoms, cyano groups, hydroxyl groups, and $C_{1-6}$ alkoxy groups.

The aryl, heteroaryl, or non-aromatic heterocyclic ring which has a substituent is preferably an aryl, heteroaryl, or non-aromatic heterocyclic ring which has one to five, and preferably one to three, substituents selected from $C_{1-6}$ alkyl groups, halogen atoms, cyano groups, hydroxyl groups, or $C_{1-6}$ alkoxy groups.

More preferred examples in General Formula (I) of the present invention include the following items <1> to <5> and any combinations thereof. The combination of all of the following items <1> to <5> is particularly preferable.

<1> $R^1$ is preferably a $C_{4-6}$ alkyl group, more preferably a 1-ethylpropyl group, an n-pentyl group, or an n-hexyl group, and particularly preferably a 1-ethylpropyl group.

<2> $R^2$ is preferably —(C=O)—$R^6$ and $R^6$ is preferably an n-butyl group, a sec-butyl group, a tert-butyl group, a benzyl group, a phenethyl group, an optionally substituted aryl group, or an optionally substituted heteroaryl group. The aryl group or heteroaryl group is preferably a phenyl group or a 5-membered to 6-membered monocyclic heteroaryl group, and more preferably a phenyl group, a pyrrolyl group, a furyl group, a thienyl group, an oxazolyl group, or a thiazolyl group, and a substituent is preferably one $C_{1-6}$ alkyl group or halogen atom or an unsubstituted group is preferable.

<3> $R^3$ and $R^4$ are preferably an amino group, —NH—(C=O)—$R^{10}$, or —NH—(C=O)—$NR^{11}R^{12}$. That is, X is preferably —$NR^{13}$—, $R^{13}$ is preferably a hydrogen atom, and $R^9$ is preferably —(C=O)—$R^{10}$ or —(C=O)—$NR^{11}R^{12}$. $R^3$ is particularly preferably an amino group, and $R^4$ is particularly preferably —NH—(C=O)—$R^{10}$ or —NH—(C=O)—$NR^{11}R^{12}$. $R^{10}$ is preferably a $C_{1-6}$ alkyl group and more preferably a methyl group, an ethyl group, an n-propyl group, an isopropyl group, a sec-butyl group, or a tert-butyl group. Regarding $R^{11}$ and $R^{12}$, a combination in which any one of $R^{11}$ and $R^{12}$ is a hydrogen atom and the other thereof is a $C_{1-6}$ alkyl group, and the $C_{1-6}$ alkyl group is preferably a $C_{1-4}$ alkyl group and particularly preferably a methyl group or an ethyl group.

<4> Q is preferably an oxygen atom.

<5> The dotted line portion is preferably a double bond.

Specific examples of particularly preferred compounds of General Formula (I) of the present invention include the following compounds:

N-[(1R,2R,6S)-6-amino-2-(1-ethylpropoxy)-4-(thiophene-2-carbonyl)-3-cyclohexen-1-yl]acetamide (Example 1);

N-[(1R,2R,6S)-6-amino-2-(1-ethylpropoxy)-4-(thiophene-2-carbonyl)-3-cyclohexen-1-yl]acetamide hydrochloride (Example 2);

N-[(1R,2R,6S)-6-amino-2-(1-ethylpropoxy)-4-(5-methyl-furan-2-carbonyl)-3-cyclohexen-1-yl]acetamide (Example 3);

N-[(1R,2R,6S)-6-amino-2-(1-ethylpropoxy)-4-(5-methylthiophene-2-carbonyl)-3-cyclohexen-1-yl]acetamide (Example 4);

N-[(1R,2R,6S)-6-amino-2-(1-ethylpropoxy)-4-(4-fluorobenzoyl)-3-cyclohexen-1-yl]acetamide (Example 5);

N-[(1R,2R,6S)-6-amino-4-benzoyl-2-(1-ethylpropoxy)-3-cyclohexen-1-yl]acetamide hydrochloride (Example 6);

N-[(1R,2R,6S)-6-amino-2-(1-ethylpropoxy)-4-phenylacetyl-3-cyclohexen-1-yl]acetamide (Example 7);

N-[(1R,2R,6S)-6-amino-2-(1-ethylpropoxy)-4-(furan-2-carbonyl)-3-cyclohexen-1-yl]acetamide (Example 8);

N-[(1R,2R,6S)-6-amino-2-(1-ethylpropoxy)-4-(1-methyl-1H-pyrrole-2-carbonyl)-3-cyclohexen-1-yl]acetamide (Example 9);

N-[(1R,2R,6S)-6-amino-4-(2,2-dimethylpropionyl)-2-(1-ethylpropoxy)-3-cyclohexen-1-yl]acetamide (Example 10);

N-[(1R,2R,6S)-6-amino-2-(1-ethylpropoxy)-4-(thiazole-2-carbonyl)-3-cyclohexen-1-yl]acetamide (Example 11);

N-[(1R,2R,6S)-6-amino-2-(1-ethylpropoxy)-4-pentanoyl-3-cyclohexen-1-yl]acetamide hydrochloride (Example 12);

N-[(1R,2R,6S)-6-amino-4-benzoyl-2-(1-ethylpropoxy)-3-cyclohexen-1-yl]-2,2-dimethylpropionamide (Example 17);

N-[(1S,5R,6R)-6-amino-3-benzoyl-5-(1-ethylpropoxy)-3-cyclohexen-1-yl]acetamide (Example 18);

N-[(1S,5R,6R)-6-amino-5-(1-ethylpropoxy)-3-(thiophene-2-carbonyl)-3-cyclohexen-1-yl]acetamide (Example 21);

N-[(1R,2R,6S)-6-amino-2-(1-ethylpropoxy)-4-(thiophene-2-carbonyl)-3-cyclohexen-1-yl]-3-methylbutylamide (Example 25);

[(1R,2R,6S)-6-amino-2-(1-ethylpropoxy)-4-(thiophene-2-carbonyl)cyclohexen-3-yl]-3-ethylurea (Example 27);

N-[(1R,2R,6S)-6-amino-2-(1-ethylpropoxy)-4-heptanoyl-3-cyclohexen-1-yl]acetamide (Example 28);

N-[(1R,2R,6S)-6-amino-2-(1-ethylpropoxy)-4-(thiophene-3-carbonyl)-3-cyclohexen-1-yl]acetamide (Example 29);

N-[(1R,2R,6S)-6-amino-4-cyclohexanecarbonyl-2-(1-ethylpropoxy)-3-cyclohexen-1-yl]acetamide hydrochloride (Example 30); and N-[(1R,2R,6S)-6-amino-2-(1-ethylpropoxy)-4-(5-methoxy-thiophene-2-carbonyl)-3-cyclohexen-1-yl]acetamide hydrochloride (Example 31).

In the present specification, the structural formula of a compound may represent a certain isomer for convenience; however, the present invention includes all of isomers such as geometric isomers, optical isomers based on asymmetric carbon atoms, sterical isomers, and tautomeric isomers, and isomeric mixtures which occur as a result of the structure of the compound. Thus, the structural formula of a compound is not intended to be limited to the formula described for convenience, and may be any one of the isomers or may be a mixture. Therefore, the compound of the present invention may have an asymmetric carbon atom in the molecule and may be an optical isomer and racemate; however, the compound is not intended to be limited to any one of them in the present invention, and all are included.

Further, the present invention includes a pharmaceutically acceptable salt of the compound of the present invention. Specific examples thereof include acid addition salts with inorganic acids, such as hydrochloride, hydrobromide, hydroiodide, sulfate, nitrate, and phosphate, acid addition salts with organic acids, such as formate, acetate, trichloroacetate, trifluoroacetate, propionate, oxalate, malonate, succinate, fumarate, maleate, lactate, malate, tartrate, citrate, methanesulfonate, ethanesulfonate, p-toluenesulfonate, aspartate, and glutamate; salts with inorganic bases, such as sodium salts, potassium salts, magnesium salts, calcium salts, and aluminum salts; salts with organic bases, such as methylamine, ethylamine, ethanolamine, lysine, and ornithine; and ammonium salts.

Furthermore, the present invention also includes pharmaceutically acceptable prodrugs of the compound of the present invention. A pharmaceutically acceptable prodrug means a compound which is subjected to enzymatic oxidation, reduction, or hydrolysis under the physiological conditions in a living organism and is converted to a compound (I) of the present invention. Examples of a group that forms a prodrug include the groups described in Prog. Med., 5, 2157-2161 (1985), or "Iyakuhin no Kaihatsu (Development of Pharmaceutical Products)" (Hirokawa Shoten Co., 1990) Vol. 7, Molecular Design, 163-198.

Furthermore, the present invention also includes hydrates, various solvates and crystal polymorphisms of the compound of the present invention and a pharmaceutically acceptable salt thereof. However, similarly, there are no limitations, and the present invention may include both any one single crystal form and a mixture of crystal forms.

Furthermore, the present invention includes compounds obtained by labeling the compound of the present invention with, for example, an isotope (for example, $^2H$, $^3H$, $^{14}C$, $^{35}S$, or $^{125}I$).

The compound of the present invention and a pharmaceutically acceptable salt thereof can be produced by applying various known synthesis methods. With regard to the introduction of substituents or conversion of functional groups, when a reactive substituent such as an amino group, a hydroxyl group or a carboxyl group is present, a desired compound can also be obtained by introducing a protective group to the relevant substituent as necessary, and removing the protective group after a target reaction is completed. The selection of the protective group, introduction of the protective group, and removal of the protective group can be appropriately selected from, for example, the methods described in Greene and Wuts, "Protective Groups in Organic Synthesis (Third Edition)" (WILEY) and carried out.

Examples of the method for producing the compound of General Formula (I) of the present invention include methods described in the following Schemes 1 to 3. However, the method for producing the compound of the present invention is not intended to be limited to these methods. A starting material in each scheme is available in the market, or can be produced by a method described in Reference Example or a known method of the related art.

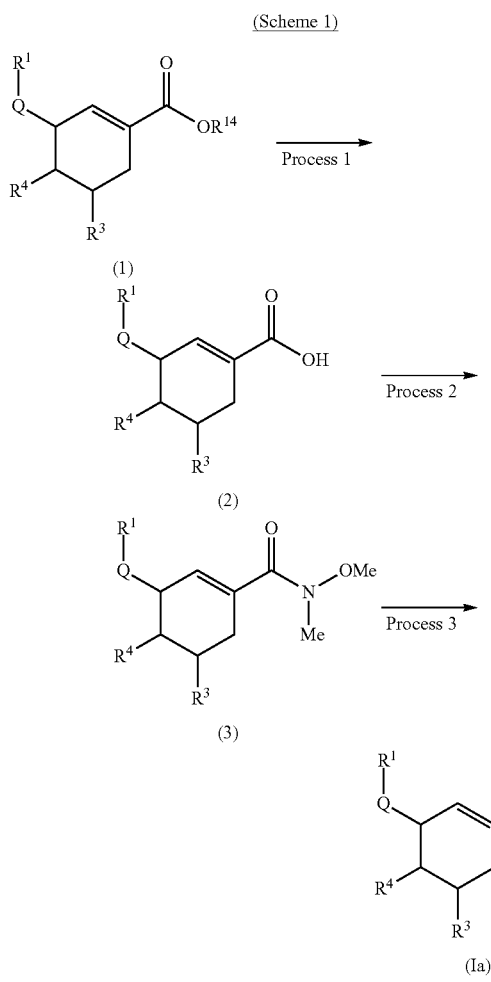

wherein $R^1$, $R^3$, $R^4$, $R^6$, and Q are defined as above General Formula (I), and $R^{14}$ represents a $C_{1-6}$ alkyl group.

A compound (Ia) of the invention of the present application described above can be synthesized according to Scheme 1.

(Process 1)

A compound (2) can be produced by ester hydrolysis of the compound (1). The hydrolysis reaction may be performed under general conditions, and can be carried out, for example, in such a manner that the compound (1) is dissolved in, for example, methanol, ethanol, tetrahydrofuran (THF), dioxane, or acetone, an aqueous solution of an alkali metal hydroxide such as lithium hydroxide, sodium hydroxide, or potassium hydroxide is then added, and the reaction is carried out for 0.5 to 100 hours at 0° C. to room temperature.

Incidentally, the compound (1) is available in the market, or can be synthesized according to a known method, for example, a method described in JP 2006-36770 A or Document (Journal of American Chemical Society, (USA), 1997, Vol. 119, p. 691-697).

(Process 2)

A compound (3) can be produced by Weinreb amidation of the compound (2) with N,O-dimethylhydroxylamine or hydrochloride thereof. The Weinreb amidation reaction can be carried out, for example, in such a manner that the compound (2) is dissolved in, for example, dichloromethane, chloroform, N,N-dimethylformamide (DMF), or THF, a condensing agent such as dicyclohexylcarbodiimide (DCC), 1-ethyl-3-(3-dimethylaminopropyl)carbodiimide hydrochloride (EDC.HCl), (benzotriazol-1-yloxy)tripyrrolidinophosphonium hexafluorophosphate (PyBOP), or 2-(1H-7-azabenzotriazol-1-yl)-1,1,3,3-tetramethyluronium hexafluorophosphate (HATU) is then added thereto, N,O-dimethylhydroxylamine or hydrochloride thereof is then added thereto, and the reaction is carried out for 0.5 to 100 hours at 0° C. to reflux temperature in the presence or absence of a base such as pyridine, triethylamine, or N,N-diisopropylethylamine.

(Process 3)

The compound (Ia) can be produced by reaction of the compound (3) with an organic metal reagent, such as an alkyllithium reagent, an aryllithium reagent, a heteroaryllithium reagent, or a Grignard reagent, in an inactive solvent. This reaction can be carried out, for example, in such a manner that the compound (3) is dissolved in, for example, THF or diethyl ether, an organic metal reagent, which is available in the market or is separately prepared by a general method, is then added, and the reaction is carried out for 0.5 to 24 hours at −78° C. to room temperature.

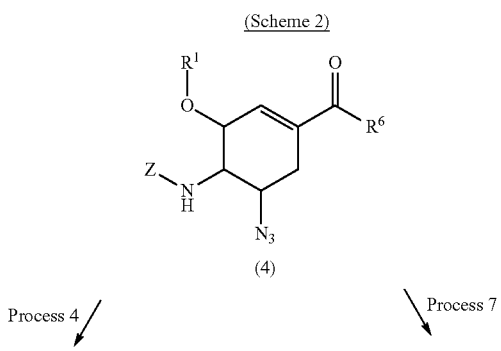

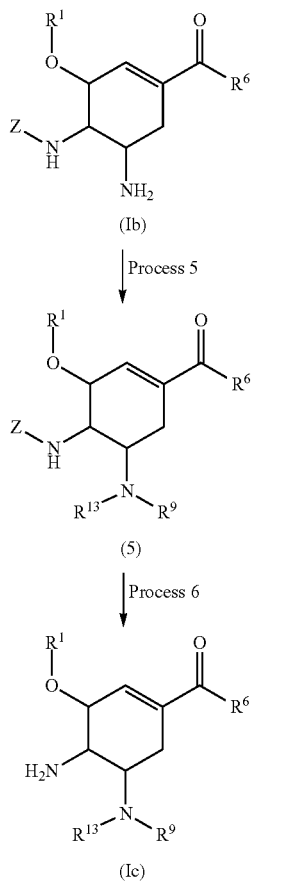
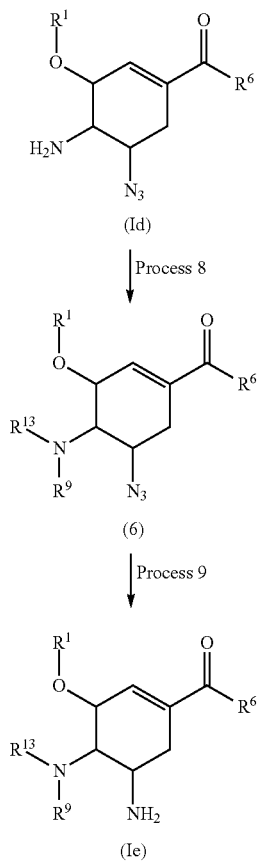

wherein $R^1$, $R^6$, $R^9$, and $R^{13}$ have the same meanings as described above, and Z represents a protective group.

A compound (Ib), a compound (Ic), a compound (Id), and a compound (Ie) of the present invention described above can be synthesized according to Scheme 2.

(Process 4)

The compound (Ib) can be produced by Staudinger reduction of a compound (4) which can be produced according to Scheme 1. The Staudinger reduction can be carried out, for example, in such a manner that the compound (4) is dissolved in a mixed solvent of water with, for example, THF, methanol, or ethanol, triphenylphosphine is then added, and the reaction is carried out for 0.5 to 48 hours at room temperature to 100° C.

(Process 5)

A compound (5) can be produced by reductive amination reaction of the compound (Ib) with an aldehyde body or a ketone body or can be produced by performing acylation reaction of the compound (Ib) with acid anhydride, acid chloride, or isocyanate once or twice as necessary. The reductive amination reaction can be carried out, for example, in such a manner that the compound (5) is dissolved in a solvent such as methanol, ethanol, diethyl ether, THF, chloroform, dichloromethane, benzene, or toluene, the aldehyde body or the ketone body is then added, the reaction is carried out in the presence or absence of a dehydrating agent such as a molecular sieve or magnesium sulfate to obtain a Schiff base, a reducing agent such as sodium borohydride, sodium cyanoborohydride, or sodium triacetoxyborohydride is then added, and the reaction is carried out for 0.5 to 48 hours at 0 to 100° C. in the presence or absence of an acid catalyst such as acetic acid. The acylation reaction can be carried out, for example, in such a manner that the compound (5) is dissolved in a solvent such as chloroform, dichloromethane, THF, benzene, or toluene, acid anhydride, acid chloride, or isocyanate is then added, and the reaction is carried out for 0.5 to 48 hours at 0 to 100° C. in the presence or absence of a base such as triethylamine, N,N-diisopropylethylamine, pyridine, or 4-dimethylaminopyridine.

(Process 6)

The compound (Ic) can be produced by deprotection of the compound (5). The deprotection method of the amino group can be appropriately selected from known methods depending on the type of the protective group. In a case where the protective group Z is a tert-butoxycarbonyl group, the deprotection can be carried out, for example, in such a manner that the compound (5) is dissolved in, for example, methanol, ethanol, 2-propanol, THF, acetonitrile, dioxane, ethyl acetate, dichloromethane, or chloroform, a hydrochloric acid solution or trifluoroacetic acid is then added, and the reaction is carried out for 0.5 to 30 hours at 0 to 100° C.

(Process 7)

The compound (Id) can be produced by deprotection of the compound (4). In this process, the same method as in Process 6 of Scheme 2 is used.

(Process 8)

A compound (6) can be produced by reductive amination reaction of the compound (Id) with an aldehyde body or a ketone body or can be produced by acylation reaction of the compound (Id) with acid anhydride or acid chloride. In this process, the same method as in Process 5 of Scheme 2 is used.

(Process 9)

The compound (Ie) can be produced by Staudinger reduction of the compound (6). In this process, the same method as in Process 4 of Scheme 2 is used.

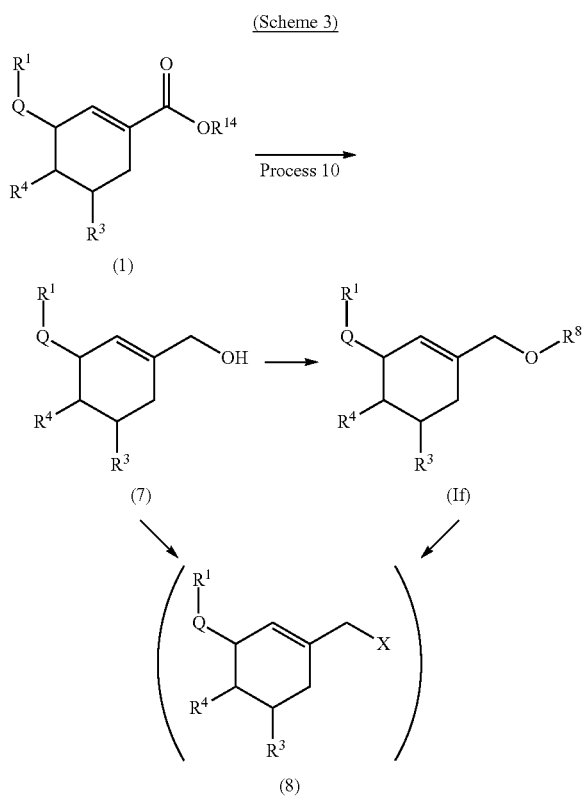

(Scheme 3)

wherein $R^1$, $R^3$, $R^4$, Q, $R^8$, and $R^{14}$ are defined as described above, and X represents a halogen atom.

A compound (If) of the present invention described above can be synthesized according to Scheme 3.

(Process 10)

A compound (7) can be produced by reducing the ester group of the compound (1) with, for example, diisobutylaluminum hydride (DIBAL). The reduction reaction can be carried out, for example, in such a manner that the compound (1) is dissolved in a solvent such as diethyl ether, THF, chloroform, or dichloromethane, a reducing agent such as DIBAL is then added, and the reaction is carried out for 0.5 to 24 hours at −78° C. to room temperature.

(Process 11)

The compound (If) can be produced by alkylation of the compound (7) or can be produced by halogenation of the compound (7) through, for example, Appel reaction to prepare a compound (8) and then etherifying the compound (8) with metal alkoxide.

The alkylation reaction of the compound (7) can be carried out, for example, in such a manner that the compound (7) is dissolved in a solvent such as diethyl ether, THF, or DMF, a metal base such as sodium hydride is then added, and the reaction is carried out for 0.5 to 24 hours at 0 to 100° C. in the presence of an alkyl halide such as iodomethane or iodoethane and in the presence or absence of a quaternary ammonium salt such as tetrabutylammonium iodide.

The halogenation reaction from the compound (7) to the compound (8) can be carried out, for example, in such a manner that the compound (7) is dissolved in a solvent such as dichloromethane or chloroform, carbon tetrachloride, triphosgene, or carbon tetrabromide is then added in the presence of triphenylphosphine, and the reaction is carried out for 0.5 to 24 hours at 0 to 100° C. The etherification reaction of the compound (8) can be carried out, for example, in such a manner that the compound (8) is dissolved in a solvent such as methanol or ethanol, sodium methoxide or sodium ethoxide is then added, and the reaction is carried out for 0.5 to 24 hours at 0 to 100° C.

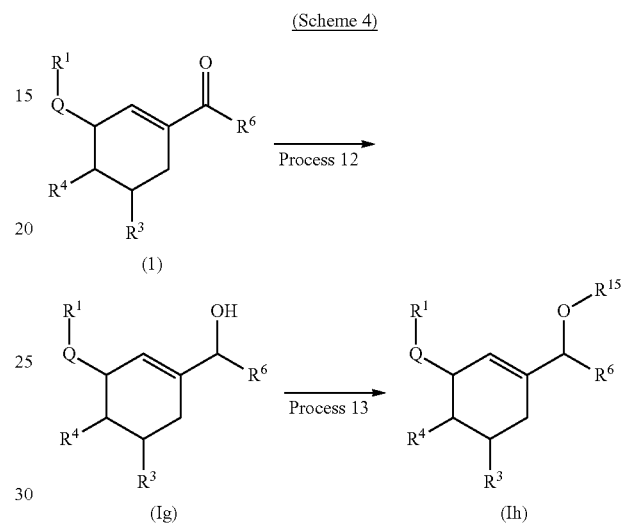

(Scheme 4)

wherein $R^1$, $R^3$, $R^4$, $R^6$, and Q are defined as described above, and $R^{15}$ represents a $C_{1-6}$ alkyl group which are optionally substituted.

A compound (Ig) and a compound (Ih) of the present invention described above can be synthesized according to Scheme 4.

(Process 12)

The compound (Ig) can be produced by Luche reduction of the compound (1). The Luche reduction can be carried out, for example, in such a manner that the compound (1) is dissolved in a solvent such as methanol or ethanol, a reducing agent such as sodium borohydride is then added thereto in the presence of a lanthanoid metal salt such as cerium (III) chloride, and the reaction is carried out for 0.5 to 24 hours at −40° C. to room temperature.

(Process 13)

The compound (Ih) can be produced by alkylation of the compound (Ig). In this process, the same method as in Process 11 of Scheme 3 is used.

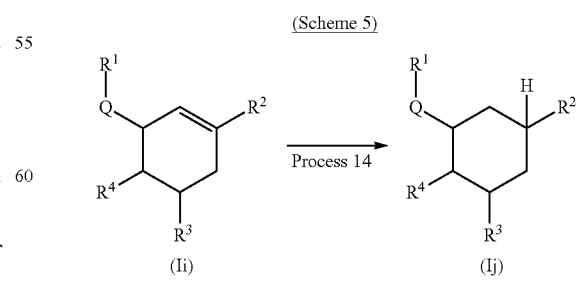

(Scheme 5)

wherein $R^1$, $R^2$, $R^3$, $R^4$, and Q are defined as described above.

A compound (Ij) of the present invention described above can be synthesized according to Scheme 4.
(Process 14)

The compound (Ij) can be produced by catalytic hydrogenation reaction of the compound (Ii) or hydride reduction reaction of the compound (Ii) with metal hydride. The catalytic hydrogenation reaction can be carried out, for example, in such a manner that the compound (Ii) is dissolved in a solvent such as methanol, ethanol, ethyl acetate, or THF, a catalyst such as palladium, palladium hydroxide, or platinum oxide (Adams catalyst) is then added, and the reaction is carried out for 0.5 to 48 hours under 1 to 5 atm and at room temperature to 100° C. under hydrogen atmosphere. The hydride reduction reaction can be carried out, for example, in such a manner that the compound (Ii) is dissolved in a solvent such as THF, dichloromethane, or chloroform, metal hydride such as sodium borohydride or lithium aluminum hydride is then added, and the reaction is carried out for 0.5 to 48 hours at 0 to 100° C.

The compounds of General Formula (I) obtained in this way have, as described in Test Example below, an excellent atrial effective refractory period prolonging effect, a weak anti-neuraminidase activity, and high safety. Therefore, the compound of the present invention is useful as a defibrillation agent and a prophylactic or therapeutic agent against arrhythmia such as atrial fibrillation or atrial flutter.

The pharmaceutical agent composition containing the compound of the present invention or a pharmaceutically acceptable salt thereof as an active ingredient can be prepared by using one or more kinds of the compound of the present invention and a pharmaceutical carrier, an excipient, or another additive, which is generally used for formulation, according to a method, which is generally used. Administration may be achieved by any form of oral administration by tablets, pills, capsules, granules, powders, or liquids and parenteral administration by injections (for example, intravenous injection or intramuscular injection), suppositories, transnasal agents, transmucosal agents, percutaneous agents, or inhalation agents. The amount of administration is appropriately determined according to individual cases in consideration of, for example, the disease or symptom to be treated, the age, body weight or gender of the subject of administration. In general, in the case of oral administration, the amount of administration of the compound of the present invention to an adult (weight: about 60 kg) per day is suitably about 1 mg to 1000 mg, preferably about 3 mg to 300 mg, and more preferably about 10 mg to 200 mg and this is administered once or in 2 to 4 divided doses. Furthermore, in the case of intravenous administration depending on the symptom, usually, the amount of administration of the compound of the present invention to an adult per day is suitably about 0.01 mg to 100 mg, preferably about 0.01 mg to about 50 mg, and more preferably about 0.01 mg to about 20 mg, per kilogram of the weight, and this is administered once or in multiple divided doses a day. Furthermore, the pharmaceutical agent composition containing the compound of the present invention may appropriately contain other anti-arrhythmic agents or active ingredients of different types, as long as the purpose of the present invention is not contradicted.

Examples of solid compositions for oral administration according to the present invention include tablets, powders, and granules. Such a solid composition can be prepared by mixing one or more kinds of active ingredients with at least one inert excipient, for example, lactose, mannitol, glucose, hydroxypropyl cellulose, fine crystalline cellulose, starch, polyvinylpyrrolidone, or magnesium metasilicate aluminate.

The solid composition may contain an additive other than the inert excipient, for example, a lubricating agent, a disintegrant, a stabilizing agent, a solubilizing agent, or a dissolution aid, according to a general method. The tablets or pills may be coated with, for example, a sugar coating or a gastric or enteral film of sucrose, gelatin, hydroxypropyl cellulose, or hydroxypropylmethyl cellulose phthalate, as necessary.

The liquid composition for oral administration can contain, for example, an emulsion, a solution, a suspension, a syrup, or an elixir which is pharmaceutically acceptable and can contain an inert diluent that is generally used, for example, purified water or ethanol. The composition may also contain an additive other than an inert diluent, for example, an auxiliary agent such as a wetting agent or a suspending agent, a sweetening agent, a flavoring agent, an aromatic agent, or an antiseptic.

The injection for parenteral administration can contain a sterile, aqueous or non-aqueous solution, suspension, or emulsion. A water-soluble solution or suspension can contain, for example, as a diluent, distilled water for injection and physiological saline. A non-water-soluble solution or suspension can contain, for example, as a diluent, propylene glycol, polyethylene glycol, a plant oil such as olive oil, an alcohol such as ethanol, or Polysorbate 80. Such a composition may further contain an auxiliary agent such as an antiseptic, a wetting agent, an emulsifier, a dispersing agent, a stabilizing agent, a solubilizing agent, or a dissolution aid. These can be sterilized by, for example, filtration through a bacteria-retaining filter, incorporation of a disinfectant, or irradiation. Furthermore, a sterile solid composition can be prepared and dissolved in sterile water or a sterile solvent for injection before use, and the resulting solution can also be used.

EXAMPLES

Hereinafter, the present invention will be described by means of Examples. However, the present invention is not limited thereto.

Reference Example 1

N-[(1S,5R,6R)-6-acetylamino-5-(1-ethylpropoxy)-3-(methoxymethylcarbamoyl)-3-cyclohexen-1-yl]carbamic acid tert-butyl ester

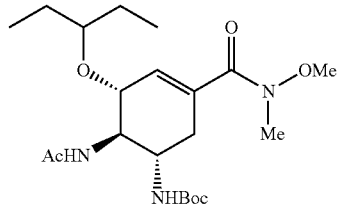 [SMILES: CCC(CC)O[C@@H]1C=C(C(=O)N(C)OC)C[C@H](NC(=O)OC(C)(C)C)[C@H]1NC(C)=O]

(3R,4R,5S)-4-Acetylamino-5-tert-butylcarbonylamino-3-(1-ethylpropoxy)-1-cyclohexen-1-carboxylic acid (1.69 g) was dissolved in DMF (20 mL), HATU (2.0 g), N,O-dimethyl hydroxylamine hydrochloride (643 mg), and N,N-diisopropylethylamine (1.70 g) were sequentially added, and the reaction mixture was stirred overnight at room temperature. The solvent was distilled off under reduced pressure, and the obtained residue was purified by silica gel column chromatography (2 to 20% methanol/chloroform) to yield a title compound (1.72 g) as a colorless solid.

¹H-NMR (CDCl₃) δ:
0.90 (3H, t, J=7.4 Hz), 0.91 (3H, t, J=7.4 Hz), 1.42 (9H, s), 1.43-1.55 (4H, m), 1.99 (3H, s), 2.37-2.50 (1H, m), 2.60-2.70 (1H, m), 3.23 (3H, s), 3.29-3.36 (1H, m), 3.65 (3H, s), 3.76-3.93 (2H, m), 4.08-4.18 (1H, m), 5.18 (1H, d, J=8.6 Hz), 5.70 (1H, d, J=9.0 Hz), 6.09-6.15 (1H, m).
ESI-MS Found: m/z 428 (M+H)⁺

Reference Example 2

N-[(1R,2R,6S)-6-azido-2-(1-ethylpropoxy)-4-hydroxymethyl-3-cyclohexen-1-yl]acetamide

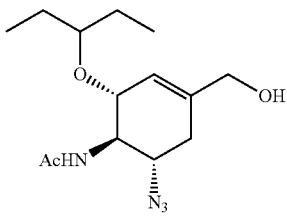 [SMILES: CCC(CC)O[C@@H]1C=C(CO)C[C@H](N=[N+]=[N-])[C@H]1NC(C)=O]

(3R,4R,5S)-4-acetylamino-5-azido-3-(1-ethylpropoxy)-1-cyclohexen-1-carboxylic acid ethyl ester (100 mg) was dissolved in dichloromethane (3 mL), 1 mol/L of DIBAL (hexane solution) (740 μL) was added dropwise under cooling at −78° C., and the reaction mixture was stirred for 110 minutes at the same temperature. 1 mol/L of DIBAL (hexane solution) (147 μL) was added, the reaction mixture was stirred for 30 minutes at the same temperature, and then the temperature thereof was raised to −40° C. over 2 hours. Methanol (1 mL) and a saturated Rochelle salt aqueous solution (1 mL) were added to the reaction mixture, the temperature of the mixture was raised to room temperature, and then the mixture was extracted with chloroform. The organic layer was dried with anhydrous sodium sulfate, and the solvent was distilled off under reduced pressure. The obtained residue was purified by silica gel column chromatography (25 to 100% ethyl acetate/hexane) to yield a colorless solid title compound (54 mg).
¹H-NMR (CDCl₃) δ: 0.89 (3H, t, J=7.6 Hz), 0.90 (3H, t, J=7.6 Hz), 1.38-1.58 (4H, m), 2.04 (3H, s), 2.04-2.19 (1H, m), 2.46 (1H, dd, J=5.6, 17.1 Hz), 3.24-3.43 (2H, m), 4.04 (2H, s), 4.27 (1H, td, J=5.9, 10.6 Hz), 4.41 (1H, d, J=8.2 Hz), 5.60-5.73 (2H, m).
ESI-MS Found: 297 (M+H)⁺

Reference Example 3

N-[(1S,5R,6R)-6-acetylamino-3-benzoyl-5-(1-ethylpropoxy)-3-cyclohexen-1-yl]carbamic acid tert-butyl ester

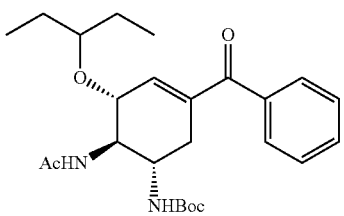 [SMILES: CCC(CC)O[C@@H]1C=C(C(=O)c2ccccc2)C[C@H](NC(=O)OC(C)(C)C)[C@H]1NC(C)=O]

The compound of Reference Example 1 (2.14 g) was dissolved in THF (42 mL), 1.08 mol/L of phenyllithium (cyclohexane-diethyl ether solution) (18.5 mL) was added dropwise under cooling at −78° C., and the reaction mixture was stirred for 2 hours at the same temperature and for 1 hour at −60° C. A saturated aqueous ammonium chloride solution was added to the reaction solution, the temperature of the mixture was raised to room temperature, and then the mixture was extracted with ethyl acetate. The organic layer was dried with anhydrous sodium sulfate, and the solvent was distilled off under reduced pressure. The obtained residue was purified by silica gel column chromatography (17 to 50% ethyl acetate/hexane) to yield a colorless solid title compound (1.25 g).
¹H-NMR (CDCl₃) δ: 0.82 (3H, t, J=6.6 Hz), 0.87 (3H, t, J=6.6 Hz), 1.38-1.54 (4H, m), 1.44 (9H, s), 2.00 (3H, s), 2.25-2.40 (1H, m), 3.02 (1H, dd, J=4.9, 17.7 Hz), 3.21-3.30 (1H, m), 3.79-3.94 (1H, m), 3.97-4.05 (1H, m), 4.10-4.24 (1H, m), 5.04 (1H, d, J=9.0 Hz), 5.90 (1H, d, J=9.2 Hz), 6.33-6.36 (1H, m), 7.38-7.47 (2H, m), 7.50-7.58 (1H, m), 7.69 (2H, d, J=7.0 Hz).
ESI-MS Found: 445 (M+H)⁺

Reference Example 4

N-[(1S,5R,6R)-6-acetylamino-5-(1-ethylpropoxy)-3-pentanoyl-3-cyclohexen-1-yl]carbamic acid tert-butyl ester

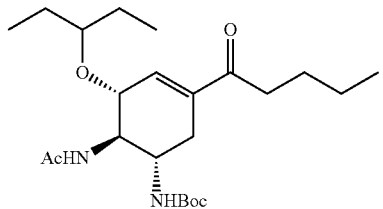 [SMILES: CCCCC(=O)C1=C[C@@H](OC(CC)CC)[C@H](NC(C)=O)[C@@H](NC(=O)OC(C)(C)C)C1]

The compound of Reference Example 1 (150 mg) was dissolved in THF (2 mL), 2.6 mol/L of n-butyllithium (hexane solution) (840 μL) was added dropwise under cooling at −78° C., and the reaction mixture was stirred for 2 hours at the same temperature. A saturated aqueous ammonium chloride solution was added to the reaction solution, the temperature of the mixture was raised to room temperature, and then the mixture was extracted with ethyl acetate. The organic layer was dried with anhydrous sodium sulfate, and the solvent was distilled off under reduced pressure. The obtained residue was purified by silica gel column chromatography (20 to 100% ethyl acetate/hexane) to yield a colorless solid title compound (121 mg).
¹H-NMR (CDCl₃) δ: 0.84-0.97 (9H, m), 1.26-1.38 (2H, m), 1.42 (9H, s), 1.45-1.64 (8H, m), 1.99 (3H, s), 2.06-2.22 (1H, m), 2.79 (1H, dd, J=5.3, 17.6 Hz), 3.35 (1H, t, J=5.7 Hz), 3.68-3.82 (1H, m), 3.95-4.12 (2H, m), 4.92 (1H, d, J=9.0 Hz), 5.77 (1H, d, J=9.0 Hz), 6.33 (1H, s).
ESI-MS Found: 425 (M+H)⁺

Reference Example 5

N-[(1R,2R,6S)-6-azido-2-(1-ethylpropoxy)-4-(methoxymethylcarbamoyl)-3-cyclohexen-1-yl]carbamic acid tert-butyl ester

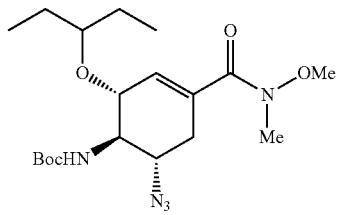 [SMILES: CCC(CC)O[C@@H]1C=C(C(=O)N(C)OC)C[C@H](N=[N+]=[N-])[C@H]1NC(=O)OC(C)(C)C]

(3R,4R,5S)-5-azido-4-tert-butoxycarbonylamino-3-(1-ethylpropoxy)-1-cyclohexen-1-carboxylic acid (3.2 g) was dissolved in DMF (87 mL), and PyBOP (5.4 g) and N,O-dimethyl hydroxylamine hydrochloride (1.3 g) was added. After ice cooling, triethylamine (3.6 mL) was added, and the reaction mixture was stirred for 3 hours at room temperature. The solvent was distilled off under reduced pressure. A saturated aqueous sodium hydrogen carbonate solution and water were added to the obtained residue, and the reaction mixture was extracted with ethyl acetate. The organic layer was washed with water and saturated brine, and then was dried with anhydrous sodium sulfate, and the solvent was distilled off under reduced pressure. The obtained residue was purified by silica gel column chromatography (15 to 75% ethyl acetate/hexane) to yield a colorless solid title compound (3.4 g).

$^1$H-NMR (CDCl$_3$) δ: 0.89 (3H, t, J=7.3 Hz), 0.91 (3H, t, J=7.6 Hz), 1.44-1.59 (4H, m), 1.46 (9H, s), 2.29-2.43 (1H, m), 2.74 (1H, dd, J=5.5, 17.0 Hz), 3.23 (3H, s), 3.24-3.34 (2H, m), 3.64 (3H, s), 4.06-4.22 (1H, m), 4.30-4.42 (1H, m), 4.78-4.90 (1H, m), 6.10-6.13 (1H, m).

ESI-MS Found: m/z 446 (M+Cl)$^-$

Reference Example 6

N-[(1R,2R,6S)-6-azido-4-benzoyl-2-(1-ethylpropoxy)-3-cyclohexen-1-yl]carbamic acid tert-butyl ester

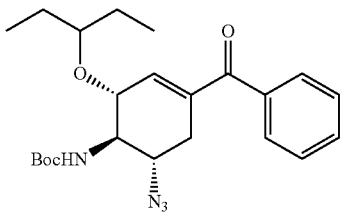 [SMILES: CCC(CC)O[C@@H]1C=C(C(=O)c2ccccc2)C[C@H](N=[N+]=[N-])[C@H]1NC(=O)OC(C)(C)C]

The compound of Reference Example 5 (1.9 g) was dissolved in THF (60 mL), 1.04 mol/L of phenyllithium (cyclohexane-diethyl ether solution) (11.6 mL) was added dropwise under cooling at −78° C., and the reaction mixture was stirred for 2 hours at the same temperature. A saturated aqueous ammonium chloride solution was added to the reaction mixture, the temperature of the mixture was raised to room temperature, and then the mixture was extracted with ethyl acetate. The organic layer was dried with anhydrous sodium sulfate, and the solvent was distilled off under reduced pressure. The obtained residue was suspended in ethanol/water (1:1) (200 mL), then collected by filtration, and washed with ethanol/water (1:1) (50 mL) to yield a yellow solid title compound (1.7 g).

$^1$H-NMR (CDCl$_3$) δ: 0.83 (3H, t, J=7.3 Hz), 0.90 (3H, t, J=7.3 Hz), 1.37-1.59 (4H, m), 1.47 (9H, s), 2.20-2.39 (1H, m), 3.09 (1H, dd, J=6.0, 17.2 Hz), 3.15-3.32 (2H, m), 4.17-4.40 (1H, m), 4.48-4.67 (1H, m), 4.85-5.07 (1H, m), 6.31-6.38 (1H, m), 7.39-7.48 (2H, m), 7.50-7.59 (1H, m), 7.64-7.74 (2H, m).

ESI-MS Found: m/z 463 (M+Cl)$^-$

Reference Example 7

N-[(1R,2R,6S)-6-acetylamino-4-benzoyl-2-(1-ethylpropoxy)-3-cyclohexen-1-yl]carbamic acid tert-butyl ester

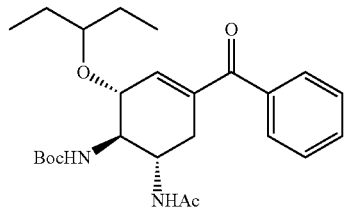 [SMILES: CCC(CC)O[C@@H]1C=C(C(=O)c2ccccc2)C[C@H](NC(C)=O)[C@H]1NC(=O)OC(C)(C)C]

The compound of Example 15 (116 mg) was dissolved in dichloromethane (6 mL), acetic anhydride (33 μL), triethylamine (80 μL), and 4-dimethylaminopyridine (7 mg) were added under ice cooling, and the reaction mixture was stirred for 10 minutes at room temperature. A saturated aqueous ammonium chloride solution was added to the reaction mixture, and then extracted with chloroform. The organic layer was dried with anhydrous sodium sulfate, and the solvent was distilled off under reduced pressure. The obtained residue was purified by silica gel column chromatography (0 to 10% methanol/chloroform) to yield a colorless solid title compound (120 mg).

$^1$H-NMR (CDCl$_3$) δ: 0.83 (3H, t, J=7.4 Hz), 0.90 (3H, t, J=7.4 Hz), 1.31-1.62 (4H, m), 1.45 (9H, s), 1.97 (3H, s), 2.26-2.47 (1H, m), 2.98 (1H, dd, J=4.5, 18.2 Hz), 3.21-3.41 (1H, m), 3.71-3.91 (1H, m), 3.95-4.06 (1H, m), 4.09-4.32 (1H, m), 4.57-4.74 (1H, m), 6.32-6.36 (1H, m), 6.40 (1H, d, J=8.6 Hz), 7.37-7.50 (2H, m), 7.50-7.59 (1H, m), 7.62-7.74 (2H, m).

ESI-MS Found: m/z 445 (M+H)$^+$

Reference Example 8

N-[(1R,2R,6S)-6-azido-2-(1-ethylpropoxy)-4-(thiophene-2-carbonyl)-3-cyclohexen-1-yl]carbamic acid tert-butyl ester

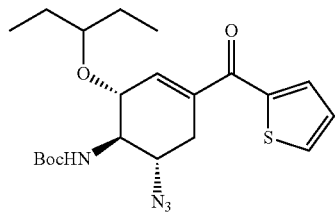 [SMILES: CCC(CC)O[C@@H]1C=C(C(=O)c2cccs2)C[C@H](N=[N+]=[N-])[C@H]1NC(=O)OC(C)(C)C]

A pale yellow amorphous title compound (1.49 g) was obtained in the same manner as in Reference Example 6 by using the compound of Reference Example 5 (1.5 g) and 2-thienyllithium (2.1 mL).

$^1$H-NMR (CDCl$_3$) δ: 0.90 (3H, t, J=7.3 Hz), 0.92 (3H, t, J=7.3 Hz), 1.47 (9H, s), 1.49-1.58 (4H, m), 2.22-2.39 (1H, m), 3.03 (1H, dd, J=5.4, 17.9 Hz), 3.13-3.27 (1H, m), 3.27-3.38 (1H, m), 4.23-4.37 (1H, m), 4.53-4.65 (1H, m), 4.89-5.00 (1H, m), 6.51-6.56 (1H, m), 7.13 (1H, dd, J=3.8, 4.9 Hz), 7.61-7.70 (2H, m).

ESI-MS Found: m/z 469 (M+Cl)$^-$

Reference Example 9

N-[(1R,2R,6S)-6-azido-4-ethoxymethyl-2-(1-ethyl-propoxy)-3-cyclohexen-1-yl]acetamide

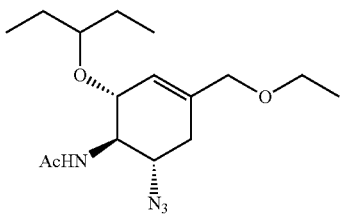 [SMILES: CCOCC1=C[C@@H](OC(CC)CC)[C@H](NC(C)=O)[C@@H](N=[N+]=[N-])C1]

The compound of Reference Example 2 (100 mg) was dissolved in THF (2 mL), sodium hydride (16 mg) was added under ice cooling, and the reaction mixture was stirred for 15 minutes at the same temperature. Iodoethane (63 mg) was added at room temperature, and the reaction mixture was stirred for 1 hour at 60° C. Iodoethane (63 mg) was added at room temperature, and the reaction mixture was stirred for 17 hours at 60° C. Sodium hydride (16 mg) was added under ice cooling, and the reaction mixture was stirred for 5 minutes at the same temperature. Iodoethane (63 mg) was added at room temperature, and the reaction mixture was stirred for 4 hours at 60° C. THF was distilled off under reduced pressure, a saturated aqueous ammonium chloride solution and water were added, and then extracted with ethyl acetate. The organic layer was dried with anhydrous sodium sulfate, and the solvent was distilled off under reduced pressure. The obtained residue was purified by silica gel column chromatography (25 to 75% ethyl acetate/hexane) to yield a yellow solid title compound (67 mg).

1H-NMR (CDCl$_3$) δ: 0.89 (6H, t, J=7.4 Hz), 1.20 (3H, t, J=7.1 Hz), 1.41-1.57 (4H, m), 2.03 (3H, s), 2.03-2.14 (1H, m), 2.50 (1H, dd, J=5.9, 17.4 Hz), 3.22-3.33 (1H, m), 3.34-3.42 (1H, m), 3.45 (2H, q, J=7.1 Hz), 3.85 (2H, s), 4.23 (1H, td, J=5.9, 10.5 Hz), 4.38 (1H, d, J=8.6 Hz), 5.60-5.70 (2H, m).

ESI-MS Found: 325 (M+H)$^+$

Reference Example 10

[(3R,4R,5S)-5-azido-4-ethylamino-3-(1-ethyl-propoxy)cyclohexen-1-yl]thiophene-2-yl-methanone

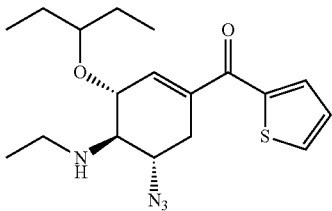 [SMILES: CCN[C@@H]1[C@@H](N=[N+]=[N-])CC(C(=O)c2cccs2)=C[C@H]1OC(CC)CC]

The compound of Example 20 (164 mg) was dissolved in dichloromethane (10 mL), magnesium sulfate (118 mg) and acetaldehyde (41 μL) were added under ice cooling, and the reaction mixture was stirred for 1 hour at the same temperature. The solvent and remaining acetaldehyde were distilled off once under reduced pressure, dichloromethane (10 mL) was then added to the obtained residue, acetic acid (84 μL) and sodium triacetoxyborohydride (415 mg) were added under ice cooling, and the reaction mixture was stirred for 0.5 hour at room temperature. A saturated aqueous sodium hydrogen carbonate solution was added to the reaction solution, and then extracted with chloroform. The organic layer was washed with saturated brine, and then was dried with anhydrous sodium sulfate, and the solvent was distilled off under reduced pressure. The obtained residue was purified by silica gel column chromatography (20 to 50% ethyl acetate/hexane) to yield a yellow oily title compound (165 mg).

$^1$H-NMR (CDCl$_3$) δ: 0.92 (3H, t, J=7.3 Hz), 0.93 (3H, t, J=7.3 Hz), 1.16 (3H, t, J=7.1 Hz), 1.45-1.68 (5H, m), 2.30-2.45 (1H, m), 2.74 (1H, dd, J=8.4, 10.4 Hz), 2.79-2.97 (2H, m), 3.03 (1H, dd, J=5.6, 17.9 Hz), 3.31-3.38 (1H, m), 3.53-3.64 (1H, m), 3.96-4.04 (1H, m), 6.55-6.59 (1H, m), 7.13 (1H, dd, J=3.8, 4.9 Hz), 7.64-7.70 (2H, m).

ESI-MS Found: 363 (M+H)$^+$

Reference Example 11

N-[(1R,2R,6S)-6-azido-2-(1-ethylpropoxy)-4-(thio-phene-2-carbonyl)-3-cyclohexen-1-yl]-N-ethylacet-amide

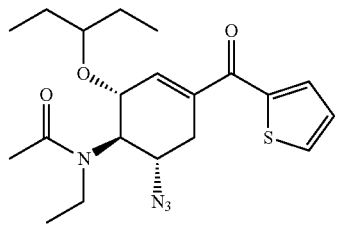 [SMILES: CCC(CC)O[C@@H]1C=C(C(=O)c2cccs2)C[C@H](N=[N+]=[N-])[C@H]1N(CC)C(C)=O]

A yellow oily title compound (69 mg) was obtained in the same manner as in Reference Example 7 by using the compound of Reference Example 10 (61 mg).

$^1$H-NMR (CDCl$_3$) δ: 0.84 (3H, t, J=7.5 Hz), 0.89 (3H, t, J=7.4 Hz), 1.31 (3H, t, J=7.2 Hz), 1.39-1.51 (4H, m), 2.14 (3H, s), 2.19-2.33 (1H, m), 2.90-3.07 (2H, m), 3.21-3.30 (1H, m), 3.34-3.57 (2H, m), 4.82-4.99 (1H, m), 5.05-5.14 (1H, m), 6.52-6.56 (1H, m), 7.13 (1H, dd, J=3.8, 4.9 Hz), 7.65-7.68 (2H, m).

ESI-MS Found: m/z 405 (M+H)$^+$

Reference Example 12

[(1R,2R,6S)-6-azido-2-(1-ethylpropoxy)-4-(thio-phene-2-carbonyl)cyclohexen-3-yl]-3-ethylurea

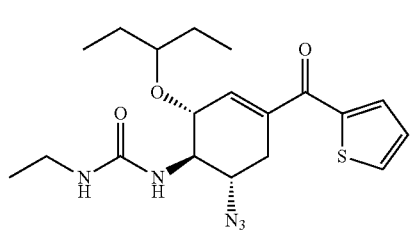 [SMILES: CCNC(=O)N[C@@H]1[C@@H](N=[N+]=[N-])CC(C(=O)c2cccs2)=C[C@H]1OC(CC)CC]

The compound of Example 20 (164 mg) was dissolved in THF (10 mL), ethyl isocyanate (157 mg) was added, and the reaction mixture was stirred for 15 hours at 50° C. The solvent was distilled off under reduced pressure, ethyl acetate was added to the obtained residue, and ultrasonic stimulation was applied. Then, the precipitated solid was collected by filtration, and the obtained solid was washed with hexane and dried under reduced pressure to yield a pale yellow solid title compound (129 mg).

$^1$H-NMR (CDCl$_3$) δ: 0.90 (3H, t, J=7.4 Hz), 0.91 (3H, t, J=7.4 Hz), 1.16 (3H, t, J=7.2 Hz), 1.44-1.57 (4H, m), 2.31-2.44 (1H, m), 3.07 (1H, dd, J=5.6, 17.7 Hz), 3.18-3.41 (4H, m), 4.18-4.31 (1H, m), 4.58 (1H, d, J=7.3 Hz), 4.66 (1H, d, J=6.8 Hz), 4.74 (1H, brs), 6.53-6.57 (1H, m), 7.14 (1H, dd, J=3.9, 4.9 Hz), 7.65-7.70 (2H, m).

ESI-MS Found: m/z 406 (M+H)$^+$

Reference Example 13

N-[(1S,5R,6R)-6-acetylamino-5-(1-ethylpropoxy)-3-hydroxymethyl-3-cyclohexen-1-yl]carbamic acid tert-butyl ester

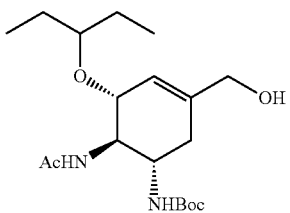 [SMILES: CCC(CC)O[C@@H]1C=C(CO)C[C@H](NC(=O)OC(C)(C)C)[C@H]1NC(C)=O]

(3R,4R,5S)-4-acetylamino-5-tert-butylcarbonylamino-3-(1-ethylpropoxy)-1-cyclohexen-1-carboxylic acid (200 mg) was dissolved in dichloromethane (2 mL), triethylamine (63 mg) was added, ethyl chloroformate (62 mg) was added under ice cooling, and the reaction mixture was stirred for 80 minutes at the same temperature. The precipitated salt was removed by filtration, the obtained filtrate was then cooled to −40° C., a solution of sodium borohydride (39 mg) in a mixed solvent of THF (1.6 mL) and methanol (0.4 mL) was slowly added, and the reaction mixture was stirred for 1 hour at the same temperature. The temperature of the reaction solution was raised to 0° C. and stirred for 10 minutes, a saturated aqueous ammonium chloride solution was added, and then extracted with chloroform. The organic layer was dried with anhydrous sodium sulfate, and the solvent was distilled off under reduced pressure. The obtained residue was purified by silica gel column chromatography (0 to 15% methanol/chloroform) to yield a colorless amorphous title compound (191 mg).

$^1$H-NMR (CDCl$_3$) δ: 0.83-0.92 (6H, m), 1.42 (9H, s), 1.44-1.56 (4H, m), 1.71 (1H, brs), 1.98 (3H, s), 2.03-2.20 (1H, m), 2.35 (1H, dd, J=5.1, 17.2 Hz), 3.30-3.37 (1H, m), 3.71-3.93 (2H, m), 3.94-4.13 (3H, m), 5.30 (1H, d, J=9.0 Hz), 5.67 (1H, s), 5.99 (H, brs).

ESI-MS Found: m/z 371 (M+H)$^+$

Reference Example 14

N-[(1S,5R,6R)-6-acetylamino-5-(1-ethylpropoxy)-3-formyl-3-cyclohexen-1-yl]carbamic acid tert-butyl ester

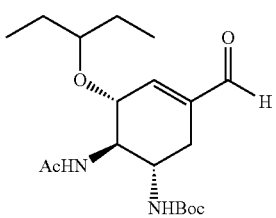 [SMILES: CCC(CC)O[C@@H]1C=C(C=O)C[C@H](NC(=O)OC(C)(C)C)[C@H]1NC(C)=O]

The compound of Reference Example 13 (926 mg) was dissolved in chloroform (13 mL), a chemically treated product of manganese (IV) oxide (2.2 g) was added, and the reaction mixture was stirred for 20 hours at 40° C. The reaction solution was diluted with chloroform and subjected to Celite filtration, and the solvent was distilled off under reduced pressure. The obtained residue was purified by silica gel column chromatography (1 to 10% methanol/chloroform) to yield a colorless solid title compound (636 mg).

$^1$H-NMR (CDCl$_3$) δ: 0.89 (3H, t, J=7.4 Hz), 0.93 (3H, t, J=7.4 Hz), 1.43 (9H, s), 1.47-1.65 (4H, m), 1.99 (3H, s), 2.03-2.23 (1H, m), 2.74 (1H, dd, J=5.2, 17.9 Hz), 3.33-3.42 (1H, m), 3.72-3.87 (1H, m), 4.03-4.18 (2H, m), 4.96 (1H, d, J=9.3 Hz), 5.80 (1H, d, J=8.1 Hz), 6.59-6.63 (1H, m), 9.50 (1H, s).

ESI-MS Found: m/z 369 (M+H)$^+$

Reference Example 15

N-[(1R,2R,6S)-6-acetylamino-2-(1-ethylpropoxy)-4-(thiophene-2-carbonyl)-3-cyclohexen-1-yl]carbamic acid tert-butyl ester

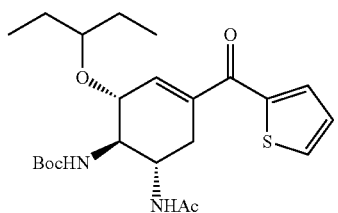 [SMILES: CCC(CC)O[C@@H]1C=C(C(=O)c2cccs2)C[C@H](NC(C)=O)[C@H]1NC(=O)OC(C)(C)C]

The compound of Reference Example 8 (198 mg) was dissolved in THF/water (4:1) (11 mL), triphenylphosphine (150 mg) was added at room temperature, and the reaction mixture was heated and stirred overnight at 40° C. The solvent was distilled off under reduced pressure, and the obtained residue was purified by silica gel column chromatography (0 to 8% methanol/chloroform) to yield a yellow amorphous form of N-[(1R,2R,6S)-6-amino-2-(1-ethylpropoxy)-4-(thiophene-2-carbonyl)-3-cyclohexen-1-yl]carbamic acid tert-butyl ester (171 mg).

The obtained N-[(1R,2R,6S)-6-amino-2-(1-ethylpropoxy)-4-(thiophene-2-carbonyl)-3-cyclohexen-1-yl]carbamic acid tert-butyl ester (171 mg) was dissolved in dichloromethane (8 mL), triethylamine (85 mL), 4-dimethylaminopyridine (10 mg), and acetic anhydride (51 mg) were sequentially added under ice cooling, and the reaction mixture was stirred for 15 minutes at the same temperature. A saturated aqueous ammonium chloride solution was added, and then extracted with chloroform. The organic layer was dried with anhydrous sodium sulfate, and the solvent was distilled off under reduced pressure. The obtained residue was purified by silica gel column chromatography (0 to 7% methanol/chloroform) to yield a yellow amorphous title compound (172 mg).

$^1$H-NMR (CDCl$_3$) δ: 0.90 (3H, t, J=7.4 Hz), 0.92 (3H, t, J=7.4 Hz), 1.43 (9H, s), 1.47-1.59 (4H, m), 1.97 (3H, s), 2.31-2.46 (1H, m), 2.93 (1H, dd, J=4.5, 18.1 Hz), 3.33-3.45 (1H, m), 3.82 (1H, dd, J=8.8, 18.7 Hz), 4.00-4.07 (1H, m), 4.13-4.28 (1H, m), 4.68 (1H, d, J=9.0 Hz), 6.42 (1H, d, J=8.6 Hz), 6.51-6.55 (1H, m), 7.13 (1H, dd, J=3.8, 4.9 Hz), 7.62-7.69 (2H, m).

ESI-MS Found: m/z 451 (M+H)$^+$

Example 1

N-[(1R,2R,6S)-6-amino-2-(1-ethylpropoxy)-4-(thiophene-2-carbonyl)-3-cyclohexen-1-yl]acetamide

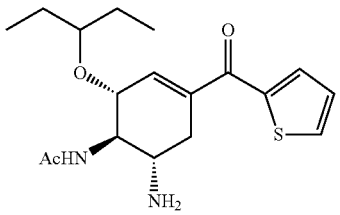

The compound of Reference Example 1 (5.0 g) was dissolved in THF (100 mL), about 1 mol/L of 2-thienyllithium (THF solution) (47 mL) was added dropwise under cooling at −78° C., and the reaction mixture was stirred for 1.5 hours at the same temperature. A saturated aqueous ammonium chloride solution was added to the reaction mixture, the temperature of the mixture was raised to room temperature, and then the mixture was extracted with ethyl acetate. The organic layer was dried with anhydrous sodium sulfate, and the solvent was distilled off under reduced pressure. The obtained residue was purified by silica gel column chromatography (15 to 100% ethyl acetate/hexane) to yield a yellow solid form of N-[(1S,5R,6R)-6-acetylamino-5-(1-ethylpropoxy)-3-(thiophene-2-carbonyl)-3-cyclohexen-1-yl]carbamic acid tert-butyl ester (4.3 g).

The obtained N-[(1S,5R,6R)-6-acetylamino-5-(1-ethylpropoxy)-3-(thiophene-2-carbonyl)-3-cyclohexen-1-yl]carbamic acid tert-butyl ester (2.06 g) was dissolved in dichloromethane (40 mL), trifluoroacetic acid (6.8 mL) was added dropwise under ice cooling, and the reaction mixture was stirred for 13 hours at room temperature. The reaction solution was distilled once under reduced pressure, a saturated aqueous sodium hydrogen carbonate solution was added to the obtained residue, and then extracted with chloroform. The organic layer was washed with saturated brine, and then was dried with anhydrous sodium sulfate, and the solvent was distilled off under reduced pressure. The obtained residue was purified by silica gel column chromatography (2 to 22% methanol/chloroform) to yield a pale yellow solid title compound (1.33 g).

$^1$H-NMR (CDCl$_3$) δ: 0.89 (3H, t, J=7.3 Hz), 0.90 (3H, t, J=7.3 Hz), 1.43-1.58 (6H, m), 2.07 (3H, s), 2.16-2.30 (1H, m), 2.96 (1H, dd, J=5.0, 17.1 Hz), 3.26-3.40 (2H, m), 3.56-3.66 (1H, m), 4.23-4.32 (1H, m), 5.59 (1H, d, J=8.1 Hz), 6.50-6.55 (1H, m), 7.13 (1H, dd, J=3.9, 4.9 Hz), 7.64-7.70 (2H, m).

ESI-MS Found: m/z 351 (M+H)$^+$

Example 2

N-[(1R,2R,6S)-6-amino-2-(1-ethylpropoxy)-4-(thiophene-2-carbonyl)-3-cyclohexen-1-yl]acetamide hydrochloride

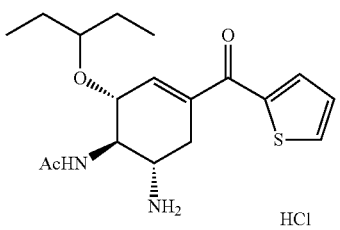 [SMILES: CCC(CC)O[C@@H]1C=C(C(=O)c2cccs2)C[C@H](N)[C@H]1NC(C)=O ; Cl]

The compound of Example 1 (1.27 g) was dissolved in a mixed solution of acetonitrile (20 mL) and methanol (2 mL), 4 mol/L of hydrogen chloride.dioxane solution (1.81 mL) was added dropwise under ice cooling, and the reaction mixture was stirred for 10 minutes at room temperature. After the reaction solution was left to stand still for 15 minutes at the same temperature, the precipitated solid was collected by filtration, washed with acetonitrile, and dried under reduced pressure to yield a colorless solid title compound (1.35 g).

$^1$H-NMR (DMSO-d$_6$) δ: 0.80 (3H, t, J=7.2 Hz), 0.82 (3H, t, J=7.3 Hz), 1.36-1.50 (4H, m), 1.91 (3H, s), 2.45-2.55 (1H, m), 2.90 (1H, dd, J=5.3, 17.0 Hz), 3.35-3.46 (2H, m), 3.81-3.92 (1H, m), 4.30 (1H, d, J=8.4 Hz), 6.55 (1H, brs), 7.28 (1H, dd, J=3.8, 5.0 Hz), 7.79 (1H, dd, J=1.0, 3.8 Hz), 8.08 (1H, dd, J=1.0, 5.0 Hz), 8.13-8.20 (3H, m).

ESI-MS Found: m/z 351 (M+H)$^+$

Example 3

N-[(1R,2R,6S)-6-amino-2-(1-ethylpropoxy)-4-(5-methylfuran-2-carbonyl)-3-cyclohexen-1-yl]acetamide

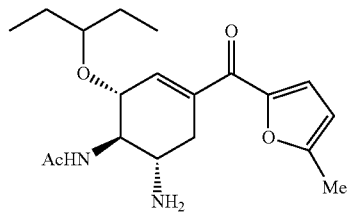 [SMILES: CCC(CC)O[C@@H]1C=C(C(=O)c2ccc(C)o2)C[C@H](N)[C@H]1NC(C)=O]

2-Methylfuran (288 mg) was dissolved in THF (5 mL), 2.65 mol/L of n-butyllithium (hexane solution) (1.05 mL) was added dropwise under cooling at −78° C., the reaction mixture was stirred for 30 minutes at room temperature. A THF solution (1 mL) of the compound of Reference Example 1 (100 mg) was added to the reaction solution under cooling at −78° C., and the reaction mixture was stirred for 2 hours at the same temperature. A saturated aqueous ammonium chloride solution was added to the reaction mixture, the temperature of the mixture was raised to room temperature, and then the mixture was extracted with ethyl acetate. The organic layer was dried with anhydrous sodium sulfate, and the solvent was distilled off under reduced pressure. The obtained residue was purified by silica gel column chromatography (15 to 100% ethyl acetate/hexane) to yield a colorless solid form of N-[(1S,5R,6R)-6-acetylamino-5-(1-ethylpropoxy)-3-(5-methylfuran-2-carbonyl)-3-cyclohexen-1-yl]carbamic acid tert-butyl ester (91 mg).

The obtained N-[(1S,5R,6R) 6-acetylamino-5-(1-ethylpropoxy)-3-(5-methylfuran-2-carbonyl)-3-cyclohexen-1-yl] carbamic acid tert-butyl ester (85 mg) was dissolved in dichloromethane (5 mL), trifluoroacetic acid (422 μL) was added dropwise under ice cooling, and the reaction mixture was stirred for 15 hours at room temperature. The reaction solution was distilled once under reduced pressure, a saturated aqueous sodium hydrogen carbonate solution was added to the obtained residue, and then extracted with chloroform. The organic layer was washed with saturated brine and then dried with anhydrous sodium sulfate, and the solvent was distilled off under reduced pressure. The obtained residue was purified by basic silica gel column chromatography (2 to 22% methanol/chloroform) to yield a pale yellow solid title compound (46 mg).

$^1$H-NMR (CDCl$_3$) δ: 0.91 (3H, t, J=7.4 Hz), 0.92 (3H, t, J=7.4 Hz), 1.47-1.57 (6H, m), 2.06 (3H, s), 2.15-2.27 (1H, m), 2.40 (3H, s), 2.94 (1H, dd, J=5.2, 17.5 Hz), 3.25-3.35 (2H, m), 3.55-3.65 (1H, m), 4.23-4.29 (1H, m), 5.54 (1H, d, J=8.2 Hz), 6.16 (1H, d, J=3.5 Hz), 6.62-6.66 (1H, m), 7.10 (1H, d, J=3.5 Hz).

ESI-MS Found: m/z 349 (M+H)$^+$

Example 4

N-[(1R,2R,6S)-6-amino-2-(1-ethylpropoxy)-4-(5-methylthiophene-2-carbonyl)-3-cyclohexen-1-yl]acetamide

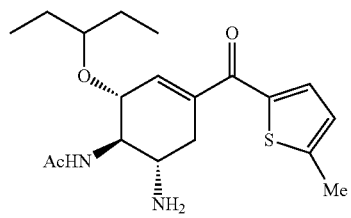

A pale yellow solid title compound (132 mg) was obtained in the same manner as in Example 3 by using the compound of Reference Example 1 (150 mg), 2-methylthiophene (517 mg), and 2.65 mol/L of n-butyllithium (hexane solution) (5.05 mmol).

$^1$H-NMR (CD$_3$OD) δ: 0.89 (6H, t, J=7.4 Hz), 1.46-1.58 (4H, m), 2.04 (3H, s), 2.33-2.46 (1H, m), 2.55 (3H, s), 2.95 (1H, dd, J=5.6, 17.3 Hz), 3.25-3.45 (2H, m), 3.94 (1H, dd, J=8.6, 11.0 Hz), 4.24 (1H, d, J=8.2 Hz), 6.51-6.55 (1H, m), 6.91 (1H, d, J=3.7 Hz), 7.59 (1H, d, J=3.7 Hz).

ESI-MS Found: m/z 365 (M+H)$^+$

Example 5

N-[(1R,2R,6S)-6-amino-2-(1-ethylpropoxy)-4-(4-fluorobenzoyl)-3-cyclohexen-1-yl]acetamide

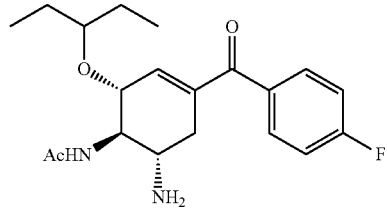 [SMILES: CCC(CC)O[C@@H]1C=C(C(=O)c2ccc(F)cc2)C[C@H](N)[C@H]1NC(C)=O]

The compound of Reference Example 1 (270 mg) was dissolved in THF (4 mL), 1.0 mol/L of 4-fluorophenylmagnesium bromide (THF solution) (5.68 mmol) was added dropwise under ice cooling, and the reaction mixture was stirred for 1.5 hours at the same temperature. A saturated aqueous ammonium chloride solution was added to the reaction solution, and the reaction mixture was extracted with ethyl acetate. The organic layer was dried with anhydrous sodium sulfate, and the solvent was distilled off under reduced pressure. The obtained residue was purified by silica gel column chromatography (25 to 100% ethyl acetate/hexane) to yield a colorless amorphous form of N-[(1S,5R,6R]-6-acetylamino-5-(1-ethylpropoxy)-3-(4-fluorobenzoyl)-3-cyclohexen-1-yl)carbamic acid tert-butyl ester (56 mg).

The obtained N-[(1S,5R,6R]-6-acetylamino-5-(1-ethylpropoxy)-3-(4-fluorobenzoyl)-3-cyclohexen-1-yl)carbamic acid tert-butyl ester (50 mg) was dissolved in dichloromethane (1 mL), trifluoroacetic acid (161 μL) was added dropwise under ice cooling, and the reaction mixture was stirred overnight at room temperature. The reaction solution was distilled once under reduced pressure, a saturated aqueous sodium hydrogen carbonate solution was added to the obtained residue, and then extracted with chloroform. The organic layer was washed with saturated brine and then dried with anhydrous sodium sulfate, the solvent was distilled off under reduced pressure. The obtained residue was purified by basic silica gel column chromatography (5 to 25% methanol/chloroform) to yield a pale yellow solid title compound (19 mg).

$^1$H-NMR (DMSO-d$_6$) δ: 0.73 (3H, t, J=6.3 Hz), 0.78 (3H, t, J=6.3 Hz), 1.26-1.45 (4H, m), 1.51 (2H, brs), 1.86 (3H, s), 1.99-2.19 (1H, m), 2.67-2.88 (2H, m), 3.21-3.29 (1H, m), 3.48-3.61 (1H, m), 4.04 (1H, d, J=8.4 Hz), 6.17-6.20 (1H, m), 7.29-7.39 (2H, m), 7.70-7.80 (3H, m).

ESI-MS Found: m/z 363 (M+H)$^+$

Example 6

N-[(1R,2R,6S)-6-amino-4-benzoyl-2-(1-ethylpropoxy)-3-cyclohexen-1-yl]acetamide hydrochloride

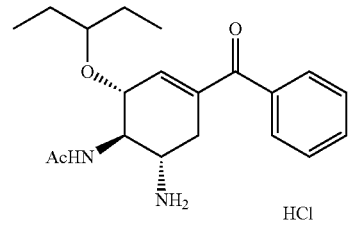 [SMILES: CCC(CC)O[C@@H]1C=C(C(=O)c2ccccc2)C[C@H](N)[C@H]1NC(C)=O ; Cl]

The compound of Reference Example 3 (1.0 g) was dissolved in 2-propanol (8 mL), concentrated hydrochloric acid (413 μL) was added, and the reaction mixture was stirred for 6 hours at 80° C. The reaction solution was cooled with ice and the precipitated crystal was collected by filtration to yield a colorless solid title compound (773 mg).

$^1$H-NMR (CD$_3$OD) δ: 0.81 (3H, t, J=7.4 Hz), 0.87 (3H, t, J=7.4 Hz), 1.37-1.57 (4H, m), 2.05 (3H, s), 2.45-2.61 (1H, m), 3.13 (1H, dd, J=5.7, 17.4 Hz), 3.29-3.41 (1H, m), 3.53-3.67 (1H, m), 4.00-4.10 (1H, m), 4.32 (1H, d, J=8.4 Hz), 6.44 (1H, m), 7.44-7.55 (2H, m), 7.57-7.66 (1H, m), 7.68-7.77 (2H, m).

ESI-MS Found: m/z 345 (M+H)$^+$

Example 7

N-[(1R,2R,6S)-6-amino-2-(1-ethylpropoxy)-4-phenylacetyl-3-cyclohexen-1-yl]acetamide

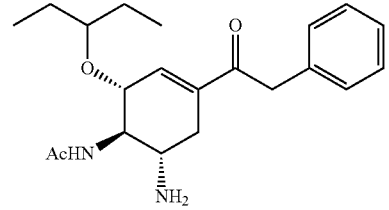 [SMILES: CCC(CC)O[C@@H]1C=C(C(=O)Cc2ccccc2)C[C@H](N)[C@H]1NC(C)=O]

A colorless amorphous title compound (56 mg) was obtained in the same manner as in Example 5 by using the compound of Reference Example 1 (150 mg) and 0.93 mol/L of benzylmagnesium chloride (THF solution) (3.51 mmol).

$^1$H-NMR (CD$_3$OD) δ: 0.89 (3H, t, J=7.4 Hz), 0.92 (3H, t, J=7.4 Hz), 1.45-1.59 (4H, m), 2.01 (3H, s), 2.12-2.25 (1H, m), 2.88 (1H, dd, J=5.4, 17.1 Hz), 3.16-3.31 (1H, m), 3.39-3.47 (1H, m), 3.81 (1H, dd, J=8.6, 11.0 Hz), 4.01 (H, d, J=15.3 Hz), 4.09 (1H, d, J=15.3 Hz), 4.19-4.25 (1H, m), 6.88-6.93 (1H, m), 7.16-7.32 (5H, m).

ESI-MS Found: m/z 359 (M+H)

Example 8

N-[(1R,2R,6S)-6-amino-2-(1-ethylpropoxy)-4-(furan-2-carbonyl)-3-cyclohexen-1-yl]acetamide

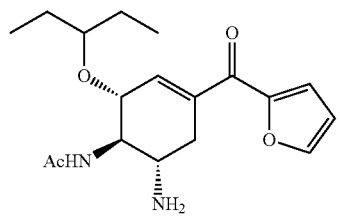

A pale yellow solid title compound (55 mg) was obtained in the same manner as in Example 3 by using the compound of Reference Example 1 (150 mg), furan (358 mg), and 2.65 mol/L of n-butyllithium (hexane solution) (4.21 mmol).

$^1$H-NMR (CDCl$_3$) δ: 0.91 (3H, t, J=7.6 Hz), 0.92 (3H, t, J=7.6 Hz), 1.46-1.59 (4H, m), 2.00 (2H, brs), 2.07 (3H, s), 2.20-2.34 (1H, m), 2.96 (1H, dd, J=4.7, 17.3 Hz), 3.28-3.41 (2H, m), 3.64 (1H, dd, J=8.5, 18.8 Hz), 4.31 (1H, d, J=8.4 Hz), 5.75-5.84 (1H, m), 6.54 (1H, dd, J=1.6, 3.5 Hz), 6.72-6.78 (1H, m), 7.19 (1H, d, J=3.5 Hz), 7.63 (1H, d, J=1.6 Hz).

ESI-MS Found: m/z 335 (M+H)$^+$

Example 9

N-[(1R,2R,6S)-6-amino-2-(1-ethylpropoxy)-4-(1-methyl-1H-pyrrole-2-carbonyl)-3-cyclohexen-1-yl]acetamide

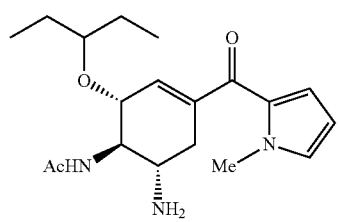 [SMILES: CCC(CC)O[C@@H]1C=C(C(=O)c2cccn2C)C[C@H](N)[C@H]1NC(C)=O]

A pale yellow solid title compound (58 mg) was obtained in the same manner as in Example 3 by using the compound of Reference Example 1 (300 mg), 1-methylpyrrole (626 mg), and tert-butyllithium (pentane solution) (7.02 mmol).

$^1$H-NMR (CDCl$_3$) δ: 0.89 (3H, t, J=7.2 Hz), 0.90 (3H, t, J=7.2 Hz), 1.44-1.64 (6H, m), 2.06 (3H, s), 2.15-2.28 (1H, m), 2.90 (1H, dd, J=5.0, 17.5 Hz), 3.23-3.36 (2H, m), 3.55-3.68 (1H, m), 3.92 (3H, s), 4.22 (1H, d, J=8.6 Hz), 5.55 (1H, d, J=7.9 Hz), 6.12 (1H, dd, J=2.6, 4.0 Hz), 6.33-6.38 (1H, m), 6.81-6.90 (2H, m).

ESI-MS Found: m/z 348 (M+H)$^+$

Example 10

N-[(1R,2R,6S)-6-amino-4-(2,2-dimethylpropionyl)-2-(1-ethylpropoxy)-3-cyclohexen-1-yl]acetamide

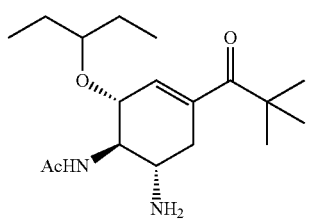

A pale yellow solid title compound (40 mg) was obtained in the same manner as in Example 1 by using the compound of Reference Example 1 (200 mg) and tert-butyllithium (2.33 mmol).

$^1$H-NMR (CDCl$_3$) δ: 0.89 (3H, t, J=7.6 Hz), 0.91 (3H, t, J=7.6 Hz), 1.25 (9H, s), 1.43-1.57 (4H, m), 2.04 (3H, s), 2.17-2.32 (1H, m), 2.50-2.80 (3H, m), 3.23-3.36 (2H, m), 3.69 (1H, dd, J=8.5, 18.8 Hz), 4.17 (1H, d, J=8.8 Hz), 6.12 (1H, brs), 6.19-6.25 (1H, m).

ESI-MS Found: m/z 325 (M+H)$^+$

Example 11

N-[(1R,2R,6S)-6-amino-2-(1-ethylpropoxy)-4-(thiazole-2-carbonyl)-3-cyclohexen-1-yl]acetamide

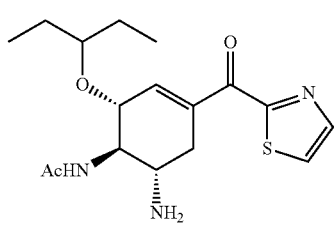 [SMILES: CCC(CC)O[C@@H]1C=C(C(=O)c2nccs2)C[C@H](N)[C@H]1NC(C)=O]

A yellow solid title compound (73 mg) was obtained in the same manner as in Example 3 by using the compound of Reference Example 1 (200 mg), thiazole (438 mg), and n-butyllithium (4.68 mmol).

$^1$H-NMR (CD$_3$OD) δ: 0.90 (3H, t, J=7.7 Hz), 0.93 (3H, t, J=7.6 Hz), 1.47-1.60 (4H, m), 2.03 (3H, s), 2.18-2.34 (1H, m), 2.88-3.00 (2H, m), 3.38-3.47 (1H, m), 3.77 (1H, dd, J=9.1, 10.4 Hz), 4.22 (1H, d, J=8.8 Hz), 7.89-7.94 (2H, m), 8.03 (1H, d, J=3.1 Hz).

ESI-MS Found: m/z 352 (M+H)$^+$

Example 12

N-[(1R,2R,6S)-6-amino-2-(1-ethylpropoxy)-4-pentanoyl-3-cyclohexen-1-yl]acetamide hydrochloride

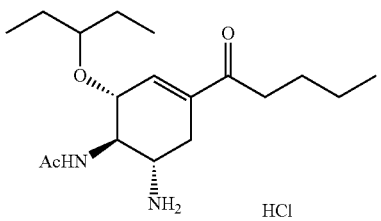 [SMILES: CCCCC(=O)C1=C[C@@H](OC(CC)CC)[C@H](NC(C)=O)[C@@H](N)C1 ; Cl]

The compound of Reference Example 4 (100 mg) was dissolved in ethyl acetate (2 mL), 4 mol/L of hydrochloric acid (ethyl acetate solution) (2 mL) was added under ice cooling, and the reaction mixture was stirred for 2 hours at room temperature. The reaction solution was distilled once under reduced pressure and then was diluted with hexane, and the precipitated crystal was collected by filtration to yield a pale yellow solid title compound (85 mg).

$^1$H-NMR (CD$_3$OD) δ: 0.85-0.98 (11H, m), 1.29-1.39 (2H, m), 1.50-1.62 (6H, m), 2.04 (3H, s), 2.23-2.35 (1H, m), 2.93 (1H, dd, J=5.3, 17.2 Hz), 3.42-3.53 (2H, m), 3.90-3.98 (1H, m), 4.29-4.35 (1H, m), 6.79-6.83 (1H, m).

ESI-MS Found: m/z 361 (M+H)$^+$

Example 13

N-[(1R,2R,6S)-6-amino-4-benzoyl-2-(1-ethylpropoxy)-3-cyclohexen-1-yl]acetamide

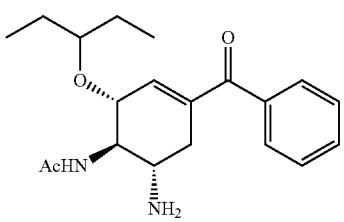 [SMILES: CCC(CC)O[C@@H]1C=C(C(=O)c2ccccc2)C[C@H](N)[C@H]1NC(C)=O]

A saturated aqueous sodium hydrogen carbonate solution was added to the compound of Example 6 (457 mg), and the reaction mixture was extracted with a mixed solution of chloroform and methanol (10:1). The organic layer was washed with saturated brine and then dried with anhydrous sodium sulfate, and the solvent was distilled off under reduced pressure. The obtained residue was purified by silica gel column chromatography (2 to 10% methanol/chloroform) to yield a colorless solid title compound (413 mg).

$^1$H-NMR (CDCl$_3$) δ: 0.83 (3H, t, J=7.4 Hz), 0.88 (3H, t, J=7.4 Hz), 1.38-1.54 (4H, m), 1.56 (2H, brs), 2.06 (3H, s), 2.14-2.28 (1H, m), 3.01 (1H, dd, J=5.3, 17.8 Hz), 3.19-3.29 (1H, m), 3.35 (1H, td, J=5.3, 10.2 Hz), 3.53-3.65 (1H, m), 4.27 (1H, d, J=8.6 Hz), 5.55 (1H, d, J=7.9 Hz), 6.32-6.36 (1H, m), 7.39-7.47 (2H, m), 7.50-7.58 (1H, m), 7.68-7.74 (2H, m).

ESI-MS Found: m/z 345 (M+H)$^+$

Example 14

[(3R,4R,5S)-4-amino-5-azido-3-(1-ethylpropoxy)-1-cyclohexen-1-yl]phenylmethanone

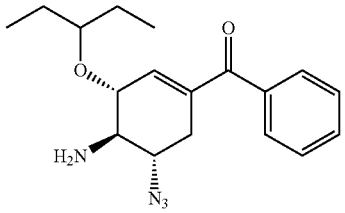

The compound of Reference Example 6 (300 mg) was dissolved in dichloromethane (7 mL), trifluoroacetic acid (1.56 mL) was added dropwise under ice cooling, and the reaction mixture was stirred for 25 hours at room temperature. The reaction solution was distilled once under reduced pressure, a saturated aqueous sodium hydrogen carbonate solution was added to the obtained residue, and then extracted with chloroform. The organic layer was dried with anhydrous sodium sulfate, the solvent was distilled off under reduced pressure. The obtained residue was purified by silica gel column chromatography (0 to 10% methanol/chloroform) to yield a bistered oily title compound (230 mg).

$^1$H-NMR (CDCl$_3$) δ: 0.84 (3H, t, J=7.3 Hz), 0.91 (3H, t, J=7.4 Hz), 1.35-1.77 (6H, m), 2.30-2.43 (1H, m), 3.00 (1H, dd, J=8.6, 10.7 Hz), 3.10-3.30 (2H, m), 3.54 (1H, td, J=5.8, 10.7 Hz), 3.88-3.97 (1H, m), 6.35-6.40 (1H, m), 7.39-7.48 (2H, m), 7.51-7.59 (1H, m), 7.64-7.75 (2H, m).

ESI-MS Found: m/z 329 (M+H)$^+$

Example 15

N-[(1R,2R,6S)-6-amino-4-benzoyl-2-(1-ethylpropoxy)-3-cyclohexen-1-yl]carbamic acid tert-butyl ester

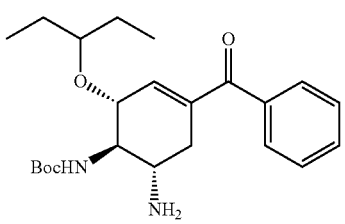

The compound of Reference Example 6 (300 mg) was dissolved in THF/water (4:1) (10 mL), triphenylphosphine (230 mg) was added at room temperature, and the reaction mixture was heated for 18 hours at 40° C. The THF was distilled off under reduced pressure, chloroform and water were added, and then extracted with chloroform. The organic layer was dried with anhydrous sodium sulfate, the solvent was distilled off under reduced pressure. The obtained residue was purified by silica gel column chromatography (0 to 10% methanol/chloroform) to yield a yellow solid title compound (274 mg).

$^1$H-NMR (CDCl$_3$) δ: 0.83 (3H, t, J=7.3 Hz), 0.90 (3H, t, J=7.4 Hz), 1.47 (9H, s), 1.36-1.62 (6H, m), 2.11-2.27 (1H, m), 3.01 (1H, dd, J=4.1, 17.7 Hz), 3.17-3.41 (3H, m), 4.12-4.26 (1H, m), 4.59-4.73 (1H, m), 6.30-6.37 (1H, m), 7.38-7.48 (2H, m), 7.49-7.58 (1H, m), 7.66-7.77 (2H, m).

ESI-MS Found: m/z 403 (M+H)$^+$

Example 16

N-[(1R,2R,6S)-6-amino-4-benzoyl-2-(1-ethyl-propoxy)-3-cyclohexen-1-yl]benzamide

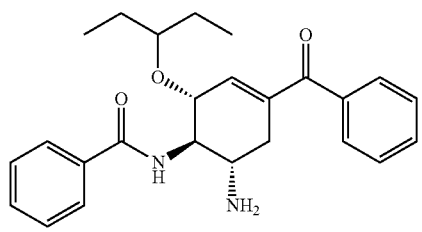 [SMILES: CCC(CC)O[C@@H]1C=C(C(=O)c2ccccc2)C[C@H](N)[C@H]1NC(=O)c1ccccc1]

The compound of Example 14 (94 mg) was dissolved in dichloromethane (6 mL), benzoyl chloride (37 μL) and triethylamine (80 μL) were added under ice cooling, and the reaction mixture was stirred for 2.5 hours at room temperature. A saturated aqueous sodium hydrogen carbonate solution was added to the reaction solution, and then extracted with chloroform. The organic layer was dried with anhydrous sodium sulfate, the solvent was distilled off under reduced pressure. The obtained residue was purified by silica gel column chromatography (5 to 35% ethyl acetate/hexane) to yield a pale yellow solid form of N-[(1R,2R,6S)-6-azido-4-benzoyl-2-(1-ethylpropoxy)-3-cyclohexen-1-yl]benzamide (97 mg). The obtained N-[(1R,2R,6S)-6-azido-4-benzoyl-2-(1-ethylpropoxy)-3-cyclohexen-1-yl]benzamide (97 mg) was dissolved in THF/water (4:1) (5 mL), triphenylphosphine (74 mg) was added at room temperature, and the reaction mixture was heated for 18 hours at 40° C. The THF was distilled off under reduced pressure, the obtained residue was diluted with chloroform, and then drying with anhydrous sodium sulfate. The solvent was distilled off under reduced pressure and the obtained residue was purified by silica gel column chromatography (0 to 10% methanol/chloroform) to yield a yellow solid title compound (58 mg).

$^1$H-NMR (CDCl$_3$) δ: 0.74 (3H, t, J=7.4 Hz), 0.81 (3H, t, J=7.4 Hz), 1.3554-1.54 (4H, m), 1.63 (2H, brs), 2.20-2.36 (1H, m), 3.05 (1H, dd, J=5.4, 17.8 Hz), 3.21-3.31 (1H, m), 3.54 (1H, td, J=5.4, 10.2 Hz), 3.71-3.85 (1H, m), 4.50 (1H, d, J=8.1 Hz), 6.34 (1H, d, J=7.7 Hz), 6.37-6.42 (1H, m), 7.40-7.49 (4H, m), 7.49-7.59 (2H, m), 7.70-7.77 (2H, m), 7.77-7.84 (2H, m).

ESI-MS Found: m/z 407 (M+H)$^+$

Example 17

N-[(1R,2R,6S)-6-amino-4-benzoyl-2-(1-ethyl-propoxy)-3-cyclohexen-1-yl]-2,2-dimethylpropionamide

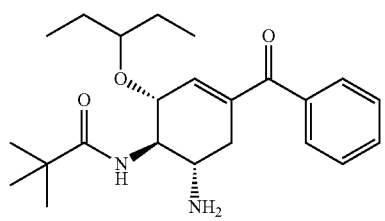 [SMILES: CCC(CC)O[C@@H]1C=C(C(=O)c2ccccc2)C[C@H](N)[C@H]1NC(=O)C(C)(C)C]

A colorless solid title compound (95 mg) was obtained in the same manner as in Example 16 by using the compound of Example 14 (112 mg) and pivaloyl chloride (46 μL).

$^1$H-NMR (CDCl$_3$) δ: 0.82 (3H, t, J=7.4 Hz), 0.86 (3H, t, J=7.4 Hz), 1.25 (9H, s), 1.35-1.57 (6H, m), 2.13-2.30 (1H, m), 2.98 (1H, dd, J=4.2, 17.2 Hz), 3.17-3.28 (1H, m), 3.39-3.58 (2H, m), 4.38 (1H, d, J=7.0 Hz), 5.78 (1H, d, J=6.2 Hz), 6.32-6.37 (1H, m), 7.38-7.47 (2H, m), 7.49-7.58 (1H, m), 7.67-7.75 (2H, m).

ESI-MS Found: m/z 387 (M+H)$^+$

Example 18

N-[(1S,5R,6R)-6-amino-3-benzoyl-5-(1-ethyl-propoxy)-3-cyclohexen-1-yl]acetamide

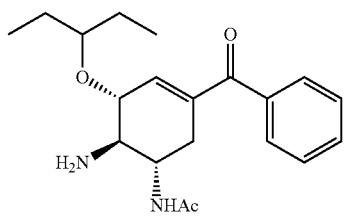 [SMILES: CCC(CC)O[C@@H]1C=C(C(=O)c2ccccc2)C[C@H](NC(C)=O)[C@H]1N]

The compound of Reference Example 7 (116 mg) was dissolved in dichloromethane (4 mL), trifluoroacetic acid (581 μL) was added dropwise under ice cooling, and the reaction mixture was stirred for 18 hours at room temperature. The reaction solution was distilled once under reduced pressure, a saturated aqueous sodium hydrogen carbonate solution was added to the obtained residue, and then extracted with chloroform. The organic layer was washed with saturated brine and then dried with anhydrous sodium sulfate, and the solvent was distilled off under reduced pressure. The obtained residue was purified by silica gel column chromatography (0 to 10% methanol/chloroform) to yield a colorless solid title compound (73 mg).

$^1$H-NMR (CDCl$_3$) δ: 0.85 (3H, t, J=7.4 Hz), 0.91 (3H, t, J=7.4 Hz), 1.38-1.65 (6H, m), 2.03 (3H, s), 2.32-2.46 (1H, m), 2.94-3.06 (2H, m), 3.26-3.36 (1H, m), 3.87-3.95 (1H, m), 4.09-4.22 (1H, m), 6.17 (1H, d, J=7.7 Hz), 6.35-6.41 (1H, m), 7.39-7.48 (2H, m), 7.50-7.59 (1H, m), 7.64-7.73 (2H, m).

ESI-MS Found: m/z 345 (M+H)$^+$

Example 19

N-[(1R,2R,6S)-6-amino-2-(1-ethylpropoxy)-4-(hydroxyphenylmethyl)-3-cyclohexen-1-yl]acetamide

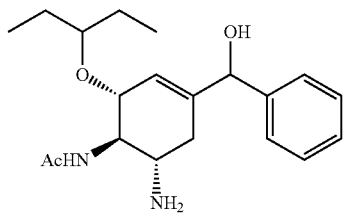

Cerium (III) chloride pentahydrate (811 mg) was dissolved in ethanol (3 mL), the reaction solution was diluted with THF (9 mL), the compound of Example 13 (300 mg) and sodium borohydride (82 mg) were added at −15° C., and the reaction mixture was stirred for 1.5 hours at the same temperature. Water was added to the reaction solution and the reaction mixture was extracted with chloroform. The organic layer was dried with anhydrous sodium sulfate, the solvent was distilled off under reduced pressure. The obtained residue was purified by basic silica gel column chromatography (2 to 22% methanol/chloroform) to yield a colorless solid title compound (80 mg).

¹H-NMR (CD₃OD) δ: 0.84-0.94 (6H, m), 1.41-1.57 (4H, m), 1.72-1.90 (1H, m), 1.99 (3H, s), 2.23 (1H, dd, J=5.5, 16.7 Hz), 2.66-2.81 (1H, m), 3.32-3.41 (1H, m), 3.57-3.70 (1H, m), 3.97 (1H, d, J=8.4 Hz), 5.03-5.08 (1H, m), 5.79-5.83 (1H, m), 7.21-7.38 (5H, m).

ESI-MS Found: m/z 381 (M+Cl)⁻

Example 20

[(3R,4R,5S)-4-amino-5-azido-3-(1-ethylpropoxy)-3-cyclohexen-1-yl]thiophene-2-yl-methanone

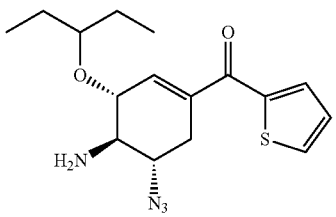 [SMILES: CCC(CC)O[C@@H]1C=C(C(=O)c2cccs2)C[C@H](N=[N+]=[N-])[C@H]1N]

A title compound (301 mg) as a yellow amorphous substance was obtained in the same manner as in Example 18 by using the compound of Reference Example 8 (400 mg) and trifluoroacetic acid (2 mL).

¹H-NMR (CDCl₃) δ: 0.93 (3H, t, J=7.6 Hz), 0.94 (3H, t, J=7.4 Hz), 1.44-1.82 (6H, m), 2.30-2.46 (1H, m), 3.00 (1H, dd, J=8.6, 10.8 Hz), 3.10 (H, dd, J=4.9, 17.1 Hz), 3.29-3.40 (1H, m), 3.55 (1H, td, J=5.7, 10.8 Hz), 3.91-4.00 (1H, m), 6.54-6.59 (1H, m), 7.14 (1H, dd, J=3.8, 4.9 Hz), 7.63-7.71 (2H, m).

ESI-MS Found: m/z 335 (M+H)⁺

Example 21

N-[(1S,5R,6R)-6-amino-5-(1-ethylpropoxy)-3-(thiophene-2-carbonyl)-3-cyclohexen-1-yl]acetamide

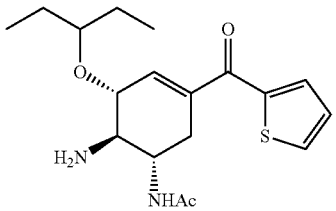 [SMILES: CCC(CC)O[C@@H]1C=C(C(=O)c2cccs2)C[C@H](NC(C)=O)[C@H]1N]

A pale white solid title compound (112 mg) was obtained in the same manner as in Example 18 by using the compound of Reference Example 15 (198 mg) and trifluoroacetic acid (28.4 μL).

¹H-NMR (CD₃OD) δ: 0.85-0.97 (6H, m), 1.42-1.71 (4H, m), 1.99 (3H, s), 2.17-2.37 (1H, m), 2.70-2.85 (1H, m), 2.85-2.97 (1H, m), 3.36-3.49 (1H, m), 3.97-4.11 (2H, m), 6.54-6.60 (1H, m), 7.15-7.22 (1H, m), 7.71-7.77 (1H, m), 7.83-7.89 (1H, m).

ESI-MS Found: m/z 351 (M+H)⁺

Example 22

N-[(1R,2R,6S)-6-amino-2-(1-ethylpropoxy)-4-(thiophene-2-carbonyl)-3-cyclohexen-1-yl]-N-ethylacetamide

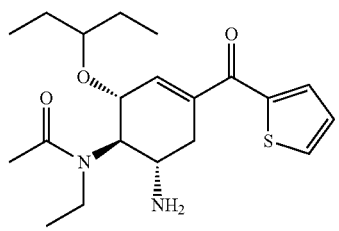 [SMILES: CCC(CC)O[C@@H]1C=C(C(=O)c2cccs2)C[C@H](N)[C@H]1N(CC)C(C)=O]

A yellow oily title compound (24 mg) was obtained in the same manner as in Example 15 by using the compound of Reference Example 11 (93 mg).

¹H-NMR (DMSO-d₆) δ: 0.69-0.89 (6H, m), 1.11-1.28 (3H, m), 1.29-1.57 (6H, m), 2.05 (3H, brs), 2.15-2.40 (1H, m), 2.59-2.84 (1H, m), 3.00-3.24 (1H, m), 3.23-3.47 (3H, m), 3.48-3.70 (1H, m), 4.20-4.36 (0.5H, m), 4.76-4.91 (0.5H, m), 6.42-6.54 (1H, m), 7.16-7.26 (1H, m), 7.67-7.78 (1H, m), 7.90-8.02 (1H, m).

ESI-MS Found: m/z 379 (M+H)⁺

Example 23

N-[(1R,2R,6S)-6-amino-4-ethoxymethyl-2-(1-ethylpropoxy)-3-cyclohexen-1-yl]acetamide

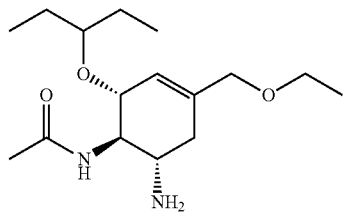

A yellow solid title compound (51 mg) was obtained in the same manner as in Example 15 by using the compound of Reference Example 9 (65 mg).

¹H-NMR (CDCl₃) δ: 0.84-0.93 (6H, m), 1.20 (3H, t, J=7.0 Hz), 1.43-1.59 (6H, m), 1.89-2.06 (1H, m), 2.04 (3H, s), 2.42 (1H, dd, J=4.2, 17.2 Hz), 3.09-3.19 (1H, m), 3.25-3.35 (1H, m), 3.46 (2H, q, J=7.0 Hz), 3.57-3.69 (1H, m), 3.86 (2H, s), 3.95-4.04 (1H, m), 5.40-5.50 (1H, m), 5.62-5.69 (1H, m).

ESI-MS Found: 299 (M+H)⁺

Example 24

N-[(1R,2S,6R)-2-amino-6-(1-ethylpropoxy)-4-(hydroxyphenylmethyl)cyclohexyl]acetamide

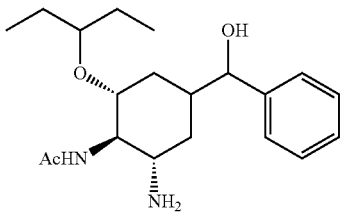

Adams catalyst (49 mg) was added to an ethanol solution (6 mL) of the compound of Example 13 (150 mg) and the reaction mixture was stirred for 1.5 hours at room temperature under a hydrogen stream (1 atm). The reaction solution was diluted with ethanol and subjected to Celite filtration, the solvent was distilled off under reduced pressure. The obtained residue was purified by basic silica gel column chromatography (2 to 22% methanol/hexane chloroform) to yield a title compound of a diastereoisomer mixture (84 mg).
ESI-MS Found: m/z 349 (M+H)$^+$

Example 25

N-[(1R,2R,6S)-6-amino-2-(1-ethylpropoxy)-4-(thiophene-2-carbonyl)-3-cyclohexen-1-yl]-3-methylbutyramide

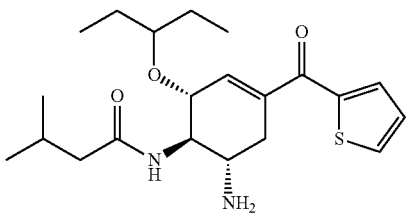 [SMILES: CCC(CC)O[C@@H]1C=C(C(=O)c2cccs2)C[C@H](N)[C@H]1NC(=O)CC(C)C]

A yellow solid title compound (65 mg) was obtained in the same manner as in Example 16 by using the compound of Example 20 (135 mg) and isovaleryl chloride (54 μL).
$^1$H-NMR (CDCl$_3$) δ: 0.89 (6H, t, J=7.3 Hz), 1.00 (6H, d, J=6.2 Hz), 1.41-1.56 (4H, m), 1.60 (2H, brs), 2.05-2.33 (4H, m), 2.95 (1H, dd, J=5.3, 17.4 Hz), 3.29-3.39 (2H, m), 3.57-3.69 (1H, m), 4.30 (1H, d, J=8.4 Hz), 5.52 (1H, d, J=7.1 Hz), 6.50-6.56 (1H, m), 7.13 (1H, dd, J=3.9, 4.9 Hz), 7.64-7.70 (2H, m).
ESI-MS Found: 393 (M+H)$^+$

Example 26

[(3R,4R,5S)-5-amino-4-ethylamino-3-(1-ethylpropoxy)cyclohexen-1-yl]thiophene-2-yl-methanone

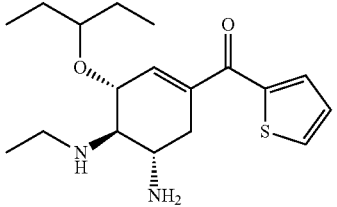

A yellow amorphous title compound (23 mg) was obtained in the same manner as in Example 15 by using the compound of Reference Example 10 (90 mg).
$^1$H-NMR (CDCl$_3$) δ: 0.92 (3H, t, J=7.6 Hz), 0.93 (3H, t, J=7.6 Hz), 1.14 (3H, t, J=7.1 Hz), 1.44-1.69 (8H, m), 2.13-2.27 (1H, m), 2.56 (1H, dd, J=8.2, 9.8 Hz), 2.66-3.04 (3H, m), 3.26-3.39 (1H, m), 3.97-4.05 (1H, m), 6.55-6.59 (1H, m), 7.12 (1H, dd, J=3.8, 4.9 Hz), 7.63-7.68 (2H, m).
ESI-MS Found: 337 (M+H)$^+$

Example 27

[(1R,2R,6S)-6-amino-2-(1-ethylpropoxy)-4-(thiophene-2-carbonyl)cyclohexen-3-yl]-3-ethylurea

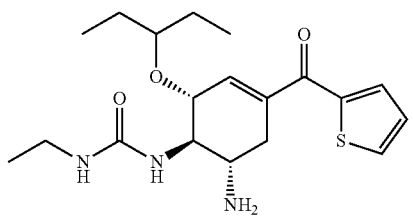 [SMILES: CCNC(=O)N[C@@H]1[C@@H](N)CC(C(=O)c2cccs2)=C[C@H]1OC(CC)CC]

A yellow amorphous title compound (54 mg) was obtained in the same manner as in Example 15 by using the compound of Reference Example 12 (90 mg).
$^1$H-NMR (CDCl$_3$) δ: 0.89 (3H, t, J=7.4 Hz), 0.93 (3H, t, J=7.4 Hz), 1.15 (3H, t, J=7.2 Hz), 1.39-1.67 (4H, m), 1.70 (2H, brs), 2.18-2.32 (1H, m), 2.97 (1H, dd, J=5.1, 17.2 Hz), 3.10-3.40 (5H, m), 4.15 (1H, d, J=7.7 Hz), 4.81 (1H, d, J=6.6 Hz), 5.43 (1H, brs), 6.51-6.54 (1H, m), 7.14 (1H, dd, J=4.0, 4.8 Hz), 7.66-7.70 (2H, m).
ESI-MS Found: 380 (M+H)$^+$

Example 28

N-[(1R,2R,6S)-6-amino-2-(1-ethylpropoxy)-4-heptanoyl-3-cyclohexen-1-yl]acetamide

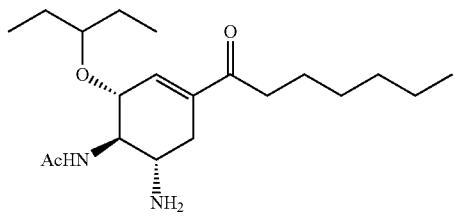 [SMILES: CCCCCCC(=O)C1=C[C@@H](OC(CC)CC)[C@H](NC(C)=O)[C@@H](N)C1]

The compound of Reference Example 1 (304 mg) was dissolved in THF (4 mL), 2.3 mol/L of n-hexyllithium (hexane solution) (3.1 mL) was added dropwise under cooling at −78° C., and the reaction mixture was stirred for 2 hours at the same temperature. A saturated aqueous ammonium chloride solution was added to the reaction mixture, the temperature of the mixture was raised to room temperature, and then the mixture was extracted with ethyl acetate. The organic layer was dried with anhydrous sodium sulfate, the solvent was distilled off under reduced pressure. The obtained residue was purified by silica gel column chromatography (20 to 70% ethyl acetate/hexane) to yield a colorless solid form of N-[(1R,2R,6S)-6-acetylamino-5-(1-ethylpropoxy)-3-heptanoyl-3-cyclohexen-1-yl]carbamic acid tert-butyl ester (154 mg). The obtained N-[(1R,2R,6S)-6-acetylamino-5-(1-ethylpropoxy)-3-heptanoyl-3-cyclohexen-1-yl]carbamic acid tert-butyl ester (153 mg) was dissolved in dichloromethane (9 mL), trifluoroacetic acid (756 μL) was added, and the reaction mixture was stirred for 15 hours at room temperature. The reaction solution was distilled once under reduced pressure, a saturated aqueous sodium hydrogen carbonate solution was added to the obtained residue, and then extracted with chloroform. The organic layer was washed with saturated brine and then dried with anhydrous sodium sulfate, and the solvent was distilled off under reduced pressure. The obtained residue was purified by silica gel column chromatography (9 to 33% methanol/chloroform) to yield a pale yellow solid title compound (55 mg).

$^1$H-NMR (CDCl$_3$) δ: 0.81-1.00 (9H, m), 1.20-1.37 (8H, m), 1.45-1.71 (4H, m), 1.96-2.11 (1H, m), 2.05 (3H, s), 2.58-2.68 (2H, m), 2.79 (1H, dd, J=5.1, 17.7 Hz), 3.18-3.30 (1H, m), 3.30-3.41 (1H, m), 3.41-3.54 (1H, m), 4.29 (1H, d, J=8.6 Hz), 5.65 (1H, d, J=7.9 Hz), 6.62 (1H, m).

ESI-MS Found: 425 (M+H)$^+$

Example 29

N-[(1R,2R,6S)-6-amino-2-(1-ethylpropoxy)-4-(thiophene-3-carbonyl)-3-cyclohexen-1-yl]acetamide

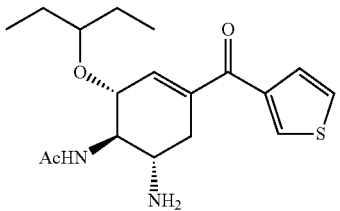 [SMILES: CCC(CC)O[C@@H]1C=C(C(=O)c2ccsc2)C[C@H](N)[C@H]1NC(C)=O]

The compound of Reference Example 1 (300 mg) was dissolved in THF (2 mL), about 0.3 mol/L of 3-thienyl magnesium iodide (THF solution) (11.6 mL) was added dropwise under cooling at −5° C., and the reaction mixture was stirred for 1 hour at the same temperature. A saturated aqueous ammonium chloride solution was added to the reaction solution, the temperature of the mixture was raised to room temperature, and then the mixture was extracted with ethyl acetate. The organic layer was dried with anhydrous sodium sulfate, and the solvent was distilled off under reduced pressure. The obtained residue was purified by silica gel column chromatography (30 to 80% ethyl acetate/hexane) to yield a yellow solid form of N-[(1S,5R,6R)-6-acetylamino-5-(1-ethylpropoxy)-3-(thiophene-3-carbonyl)-3-cyclohexen-1-yl]carbamic acid tert-butyl ester (90 mg).

The obtained N-[(1S,5R,6R)-6-acetylamino-5-(1-ethylpropoxy)-3-(thiophene-3-carbonyl)-3-cyclohexen-1-yl]carbamic acid tert-butyl ester (90 mg) was dissolved in dichloromethane (5 mL), trifluoroacetic acid (445 μL) was added dropwise, and the reaction mixture was stirred overnight at room temperature. The reaction solution was distilled once under reduced pressure, a saturated aqueous sodium hydrogen carbonate solution was added to the obtained residue, and the reaction mixture was extracted with a mixed solvent prepared by adding a small amount of methanol to chloroform. The organic layer was washed with saturated brine and then dried with anhydrous sodium sulfate, and the solvent was distilled off under reduced pressure. The obtained residue was purified by silica gel column chromatography (9 to 33% methanol/chloroform) to yield a pale yellow solid title compound (55 mg).

$^1$H-NMR (CDCl$_3$) δ: 0.88 (3H, t, J=7.3 Hz), 0.90 (3H, t, J=7.3 Hz), 1.40-1.66 (6H, m), 2.07 (3H, s), 2.13-2.30 (1H, m), 2.98 (1H, dd, J=5.0, 18.3 Hz), 3.23-3.41 (2H, m), 3.60 (1H, dd, J=8.6, 18.3 Hz), 4.28 (1H, d, J=9.7 Hz), 5.58 (1H, d, J=6.2 Hz), 6.51-6.44 (1H, m), 7.34 (1H, dd, J=2.8, 5.0 Hz), 7.48 (1H, d, J=5.0 Hz), 7.88-7.93 (1H, m).

ESI-MS Found: m/z 351 (M+H)$^+$

Example 30

N-[(1R,2R,6S)-6-amino-2-(1-ethylpropoxy)-4-(5-methoxythiophene-2-carbonyl)-3-cyclohexen-1-yl]acetamide hydrochloride

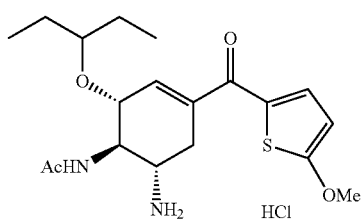 [SMILES: CCC(CC)O[C@@H]1C=C(C(=O)c2ccc(OC)s2)C[C@H](N)[C@H]1NC(C)=O ; Cl]

A brown solid form of N-[(1S,5R,6R)-6-acetylamino-5-(1-ethylpropoxy)-3-(5-methoxythiophene-2-carbonyl)-3-cyclohexen-1-yl]carbamic acid tert-butyl ester (366 mg) was obtained in the same manner as in Example 3 by using the compound of Reference Example 1 (500 mg), 2-methoxythiophene (801 mg), and 2.65 mol/L of n-butyllithium (hexane solution) (5.85 mmol).

The obtained N-[(1S,5R,6R)-6-acetylamino-5-(1-ethylpropoxy)-3-(5-methoxythiophene-2-carbonyl)-3-cyclohexen-1-yl]carbamic acid tert-butyl ester (316 mg) was dissolved in 2-propanol (2 mL), concentrated hydrochloric acid (48 mg) was added, and the reaction mixture was heated for 3 hours at 80° C. After cooling to room temperature, the mixture was diluted with ethyl acetate (2 mL) and the precipitated crystal was collected by filtration to yield a brown solid title compound (244 mg).

$^1$H-NMR (CD$_3$OD) δ: 0.90 (3H, t, J=7.4 Hz), 0.91 (3H, t, J=7.4 Hz), 1.47-1.61 (4H, m), 2.05 (3H, s), 2.45-2.58 (1H, m), 2.98 (1H, dd, J=5.5, 17.2 Hz), 3.40-3.50 (1H, m), 3.58 (1H, dt, J=5.1, 16.6 Hz), 4.00 (3H, s), 4.01-4.10 (1H, s), 4.31 (1H, d, J=8.6 Hz), 6.42 (1H, d, J=4.4 Hz), 6.45-6.49 (1H, m), 7.59 (1H, d, J=4.4 Hz).

ESI-MS Found: m/z 381 (M+H)$^+$

Example 31

N-[(1R,2R,6S)-6-amino-4-cyclohexanecarbonyl-2-(1-ethylpropoxy)-3-cyclohexen-1-yl]acetamide hydrochloride

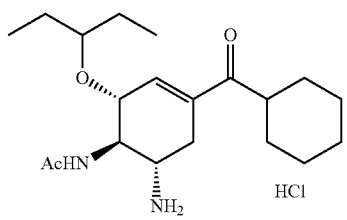 [SMILES: CCC(CC)O[C@@H]1C=C(C(=O)C2CCCCC2)C[C@H](N)[C@H]1NC(C)=O ; Cl]

The compound of Reference Example 14 (300 mg) was dissolved in THF (8 mL), 2.0 mol/L of cyclohexylmagnesium chloride (diethyl ether solution) (1.63 mmol) was added dropwise under ice cooling, and the reaction mixture was stirred for 2 hours at room temperature. A saturated aqueous ammonium chloride solution was added to the reaction solution and then extracted with ethyl acetate. The organic layer was dried with anhydrous sodium sulfate, the solvent was distilled off under reduced pressured. The obtained residue (351 mg) was dissolved in dichloromethane (7 mL), Dess-Martin periodinane (656 mg) was added, and the reaction mixture was stirred for 2.5 hours at room temperature. A saturated aqueous sodium hydrogen carbonate solution and an aqueous sodium thiosulfate solution were added to the reaction solution and then extracted with ethyl acetate. The organic layer was dried with anhydrous sodium sulfate, the solvent was distilled off under reduced pressure. The obtained residue (316 mg) was dissolved in 2-propanol (2 mL), concentrated hydrochloric acid (51 mg) was added, and the reaction mixture was heated for 24 hours at 40° C. After cooling to room temperature, the mixture was diluted with ethyl acetate (2 mL) and the precipitated crystal was collected by filtration to yield a brown solid title compound (85 mg).

$^1$H-NMR (CD$_3$OD) δ: 0.90 (3H, t, J=7.4 Hz), 0.95 (3H, t, J=7.4 Hz), 1.17-1.47 (6H, m), 1.47-1.62 (4H, m), 1.66-1.84 (4H, m), 2.03 (3H, s), 2.17-2.33 (1H, m), 2.92 (1H, dd, J=5.2, 17.3 Hz), 3.02-3.17 (1H, m), 3.40-3.55 (2H, m), 3.88-4.00 (1H, m), 4.31 (1H, d, J=8.4 Hz), 6.81-6.85 (1H, m), 8.28 (1H, d, J=8.6 Hz).

ESI-MS Found: m/z 351 (M+H)$^+$

Example 32

N-[(1R,2R,6S)-6-amino-2-(1-ethylpropoxy)-4-(hydroxythiophene-2-yl-methyl)-3-cyclohexen-1-yl]acetamide

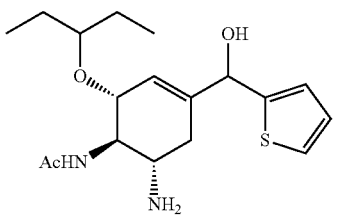 [SMILES: CCC(CC)O[C@@H]1C=C(C(O)c2cccs2)C[C@H](N)[C@H]1NC(C)=O]

A colorless solid title compound (70 mg) was obtained as a diastereoisomer mixture in the same manner as in Example 19 by using the compound of Example 1 (300 mg).

$^1$H-NMR (CDCl$_3$) δ: 0.85-0.95 (6H, m), 1.41-1.44 (2H, m), 1.45-1.56 (5H, m), 1.89-2.01 (1H, m), 2.03 (1.5H, s), 2.07 (1.5H, s), 2.10-2.36 (1H, m), 2.95 (0.5H, dd, J=5.0, 18.1 Hz), 3.04-3.16 (0.5H, m), 3.26-3.39 (1.5H, m), 3.54-3.67 (1H, m), 4.06 (0.5H, d, J=7.3 Hz), 4.29 (0.5H, d, J=8.1 Hz), 5.32-5.37 (0.5H, m), 5.47 (0.5H, d, J=7.9 Hz), 5.57 (0.5H, d, J=8.2 Hz), 5.85-5.95 (0.5H, m), 6.49-6.54 (0.5H, m), 6.92-7.01 (1.5H, m), 7.10-7.17 (0.5H, m), 7.63-7.71 (1H, m).

ESI-MS Found: m/z 353 (M+H)$^+$

Example 33

N-[(1R,2S,4S,6S)-2-amino-6-(1-ethylpropoxy)-4-(thiophene-2-carbonyl)cyclohexyl]acetamide; and N-[(1R,2S,4R,6S)-2-amino-6-(1-ethylpropoxy)-4-(thiophene-2-carbonyl)cyclohexyl]acetamide

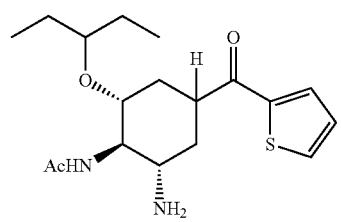 [SMILES: CCC(CC)O[C@@H]1CC(C(=O)c2cccs2)C[C@H](N)[C@H]1NC(C)=O]

The compound of Example 1 (500 mg) was dissolved in ethanol (5 mL), 5% palladium carbon (containing 55% water) (347 mg) was added, and the reaction mixture was stirred at room temperature under hydrogen atmosphere. The insoluble substance was filtered off with Celite, and then the reaction solvent was distilled off under reduced pressure. The obtained residue was purified by basic silica gel column chromatography (2 to 22% methanol/chloroform) to yield a high-polarity diastereomer 1 (189 mg) and a low-polarity diastereomer 2 (211 mg) of the title compound.

(Diastereomer 1): $^1$H-NMR (CDCl$_3$) δ: 0.88 (3H, t, J=7.4 Hz), 0.90 (3H, t, J=7.4 Hz), 1.41-1.67 (6H, m), 1.69-1.87 (2H, m), 2.02 (3H, s), 2.05-2.19 (2H, m), 2.81-2.91 (1H, m), 3.21-3.33 (1H, m), 3.68-3.87 (3H, m), 5.39-5.49 (1H, m), 7.15 (1H, dd, J=4.8, 3.2 Hz), 7.66 (1H, d, J=4.8 Hz), 7.74 (H, d, J=3.2 Hz).

ESI-MS Found: m/z 353 (M+H)$^+$ (Diastereomer 2): $^1$H-NMR (CDCl$_3$) δ: 0.85 (3H, t, J=7.6 Hz), 0.87 (3H, t, J=7.6 Hz), 1.33-1.70 (8H, m), 2.05 (3H, s), 2.09-2.30 (2H, m), 3.05-3.31 (4H, m), 3.59-3.72 (1H, m), 5.51 (1H, d, J=7.1 Hz), 7.16 (1H, dd, J=3.8, 4.9 Hz), 7.67 (1H, dd, J=1.0, 4.9 Hz), 7.73 (1H, dd, J=1.0, 3.8 Hz).

ESI-MS Found: m/z 353 (M+H)$^+$

Test Example 1

The atrial fibrillation suppression effect can be confirmed by evaluating the atrial effective refractory period (AERP) prolonging effect when the compound is administered to an atrium electrostimulation model of animals based on Patent Document 1. For representative compounds of the present invention, the AERP prolonging effect was evaluated by using rats by way of the following Test Example.

Male SD rats were subjected to intraperitoneal anesthesia with a pentobarbital sodium solution (50 mg/kg). The catheter was inserted into the artery of the lower right extremity, and the blood pressure was measured by using an amplification unit for a transducer via a pressure transducer. Further, the electrocardiogram (lead II) was measured in an amplification unit for bioelectricity by electrodes attached on four limbs via a head amplification for electrocardiogram, and the heart rate was calculated from the electrocardiographic waveform by using an instantaneous measurement unit. The blood pressure, the heart rate, and the electrocardiogram were guided to HEM and recorded. Next, the pharyngeal portion was cut, and cannulation was performed on the trachea, and then the artificial respiration was carried out using an artificial ventilator by indoor air with a tidal volume of 10 mL/kg and at 60 times/min. Furthermore, the MAP-recording and stimulating catheter for small animals was inserted into the right atrium through the cervical vein, and the atrium MAP electrocardiogram was obtained. The threshold of atrium excitation responding to electro-stimulation when electrostimulation was applied at a basic cycle of 120 ms and a duration of 6 ms by using the electrode catheter inserted into the atrium was measured, and the atrial effective refractory period (AERP) when stimulation was applied twice the threshold (about 1.0 v) was measured (basic cycle: 120 ms, duration: 6 ms, the number of times of stimulation: 10 times). Incidentally, supplemental anesthesia of pentobarbital was performed, as necessary, while the depth of anesthesia was checked for the purpose of alleviating the degree of pain of the animal so that the deep anesthesia state was maintained.

In drug assessment, the drug administration was conducted at 10 mg/kg/10 min, and then changes in the heart rate (HR), the average blood pressure (MBP), and AERP were evaluated at an interval of 5 minutes. Evaluation was carried out for three examples for each group.

Test results thereof are shown in Table 1.

TABLE 1

| Example | ΔAERP prolongation (ms) |
|---|---|
| 1 | 40.0 |
| 3 | 14.5 |
| 5 | 22.0 |
| 6 | 35.7 |
| 7 | 22.0 |
| 10 | 16.0 |
| 12 | 23.0 |
| 16 | 18.7 |
| 17 | 39.3 |
| 18 | 24.0 |
| 21 | 29.5 |
| 23 | 30.0 |
| 24 | 20.5 |
| 25 | 37.7 |
| 27 | 56.0 |
| Oseltamivir | 15.7 |

As presented in Table 1, it was found that the compound of the present invention exhibits the same or higher level of AERP prolonging effect as that of oseltamivir and has a strong atrial fibrillation suppression effect.

Further, when, with reference to the method of Sugiyama, etc. (Journal of Pharmacological Sciences, 2005, Vol. 98, p. 315-318), an electrode catheter was further inserted into the test model from the esophagus, and high-frequency electrostimulation was applied to the atrium so as to generate atrial fibrillation, the compound of the present invention suppressed the atrial fibrillation.

Test Example 2

Representative compounds of the present invention were tested on the inhibition effect against neuraminidase (H1N1) by way of the following Test Example.

For the test, EnzyChrom Neuraminidase Assay Kit (Bio-Assay Systems) and Recombinant Influenza A Virus H1N1 Neuraminidase (R&D Systems) were used.

For measurement, 30 μL of assay buffer, 55 μl of substrate, 1 μl of cofactors, 1 μl of enzyme, 0.5 μl of dye, and 15 ng of neuraminidase for each reaction sample were mixed, and 80 μL of a mixed liquid and 20 μL of a test substance solution for measurement were introduced to a 96-well microtiter plate and mixed. The plate was left to stand still for 50 minutes at 37° C. while protected from light and absorbance at 570 nm was measured by using an absorptiometer (VersaMax, Molecular Devices).

Incidentally, the control group containing no test substance was set as the high control (HC) group and the control group containing no neuraminidase was set as the low control (LC) group.

A test substance was prepared as a DMSO solution having a concentration of 1,000 times the measurement concentration, was diluted 1000-fold with pure water at the time of measurement, and this solution was used as a test substance solution for measurement.

The neuraminidase inhibition rate (%) was calculated according to the following equation.

Inhibition rate (%)=100−100*(*OD*(compound)−*OD*(LC))/(*OD*(HC)−*OD*(LC))

OD(HC): absorbance in high control group (OD 570 nm)
OD(LC): absorbance in low control group (OD 570 nm)

Further, the inhibition activity determination of each test compound at concentrations of 0.001 nM, 0.01 nM, 0.1 nM, 1, 10 nM, 100 nM, and 1000 nM was performed and the IC$_{50}$ value was calculated by using the curve fitting formula of AssayExplorer (Symyx Technologies, Inc.) (Model 08: sigmoidal inhibition curve).

Test results thereof are shown in Table 2.

TABLE 2

Neuraminidase inhibition activity

| Example | Neuraminidase inhibition activity IC$_{50}$ (nM) |
|---|---|
| 1 | 71,700 |
| 4 | 66,300 |
| 6 | 86,000 |
| 12 | 47,300 |
|  | >300,000 |
| 17 | >300,000 |
| 18 | >300,000 |
| 19 | 87,300 |
| 21 | >300,000 |
| 23 | 80,100 |
| 24 | >300,000 |
| 26 | >300,000 |
| 27 | >300,000 |
| 28 | 24,600 |
| 30 | 10,600 |
| Oseltamivir active substance | 0.78 |
| Oseltamivir (unchanged drug) | <1,000 |
| Zanamivir | 1.62 |

From Table 2, it was considered that the compound of the present invention did not almost exhibit the neuraminidase inhibition effect and did not have the antiviral effect.

The invention claimed is:

1. A compound represented by Formula (I), a pharmaceutically acceptable salt thereof, or a solvate thereof:

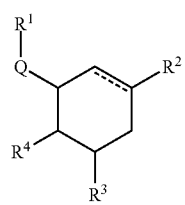

(I)

wherein the dotted line portion represents a single bond or a double bond;

R$^1$ represents an optionally substituted C$_{1-6}$ alkyl group;

Q represents an oxygen atom or a sulfur atom;

$R^2$ represents —(C=O)—$R^6$, —$CHR^6R^7$, or —$CH_2OR^8$;
$R^6$ represents an optionally substituted $C_{1-6}$ alkyl group, an optionally substituted aryl group, or an optionally substituted heteroaryl group;
$R^7$ represents a hydroxyl group or an optionally substituted $C_{1-6}$ alkoxy group;
$R^8$ represents an optionally substituted $C_{1-6}$ alkyl group;
$R^3$ and $R^4$, which may be identical or different, each represent an amino group, an azide group, or —X—$R^9$;
$R^9$ represents a hydrogen atom, an optionally substituted $C_{1-6}$ alkyl group, —(C=O)—$R^{10}$, or —(C=O)—$NR^{11}R^{12}$;
$R^{10}$ represents an optionally substituted $C_{1-6}$ alkyl group, an optionally substituted $C_{1-6}$ alkoxy group, an optionally substituted aryl group, or an optionally substituted heteroaryl group;
$R^{11}$ and $R^{12}$, which may be identical or different, each represent a hydrogen atom or an optionally substituted $C_{1-6}$ alkyl group;
X represents $NR^{13}$; and
$R^{13}$ represents a hydrogen atom, an optionally substituted $C_{1-6}$ alkyl group, or an optionally substituted non-aromatic heterocyclic ring formed by combining with $R^9$ and an adjacent nitrogen atom,
with the proviso that any one of $R^3$ and $R^4$ is an amino group.

2. The compound according to claim 1, a pharmaceutically acceptable salt thereof, or a solvate thereof, wherein the dotted line portion in Formula (I) represents a double bond.

3. A compound represented by Formula (II), a pharmaceutically acceptable salt thereof, or a solvate thereof:

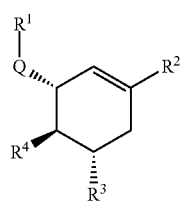

(II)

wherein
$R^1$ represents an optionally substituted $C_{1-6}$ alkyl group;
Q represents an oxygen atom or a sulfur atom;
$R^2$ represents —(C=O)—$R^6$, —$CHR^6R^7$, or —$CH_2OR^8$;
$R^6$ represents an optionally substituted $C_{1-6}$ alkyl group, an optionally substituted aryl group, or an optionally substituted heteroaryl group;
$R^7$ represents a hydroxyl group or an optionally substituted $C_{1-6}$ alkoxy group;
$R^8$ represents an optionally substituted $C_{1-6}$ alkyl group;
$R^3$ and $R^4$, which may be identical or different, each represent an amino group, an azide group, or —X—$R^9$;
$R^9$ represents a hydrogen atom, an optionally substituted $C_{1-6}$ alkyl group, —(C=O)—$R^{10}$, or —(C=O)—$NR^{11}R^{12}$;
$R^{10}$ represents an optionally substituted $C_{1-6}$ alkyl group, an optionally substituted $C_{1-6}$ alkoxy group, an optionally substituted aryl group, or an optionally substituted heteroaryl group;
$R^{11}$ and $R^{12}$, which may be identical or different, each represent a hydrogen atom or an optionally substituted $C_{1-6}$ alkyl group;
X represents $NR^{13}$; and
$R^{13}$ represents a hydrogen atom, an optionally substituted $C_{1-6}$ alkyl group, or an optionally substituted non-aromatic heterocyclic ring formed by combining with $R^9$ and an adjacent nitrogen atom,
with the proviso that any one of $R^3$ and $R^4$ is an amino group.

4. The compound according to claim 1, a pharmaceutically acceptable salt thereof, or a solvate thereof, wherein the substituent which the $C_{1-6}$ alkyl group, the aryl group, the heteroaryl group, the $C_{1-6}$ alkoxy group and the non-aromatic heterocyclic ring optionally have is one to five substituents selected from the group consisting of a halogen atom, a hydroxyl group, a cyano group, a nitro group, a $C_{1-6}$ alkyl group, a $C_{2-6}$ alkenyl group, a $C_{1-6}$ alkoxy group, an acyl group, a carboxyl group, a $C_{1-6}$ alkylcarbonylamino group, a $C_{1-6}$ alkoxycarbonyl group, a carbamoyl group, a sulfamoyl group, a $C_{1-6}$ alkylsulfanyl group, a $C_{1-6}$ alkylsulfenyl group, a $C_{1-6}$ alkylsulfonyl group, an amino group, a $C_{1-6}$ alkylamino group, a $C_{1-6}$ dialkylamino group, an aryl group, a heteroaryl group, and a non-aromatic heterocyclic ring group.

5. The compound according to claim 1, a pharmaceutically acceptable salt thereof, or a solvate thereof, wherein $R^3$ is an amino group and $R^4$ is —NH(C=O)—$R^{10}$ or —NH—(C=O)—$NR^{11}R^{12}$.

6. The compound according to claim 1, a pharmaceutically acceptable salt thereof, or a solvate thereof, which is selected from the group consisting of:
N-[(1R,2R,6S)-6-amino-2-(1-ethylpropoxy)-4-(thiophene-2-carbonyl)-3-cyclohexen-1-yl]acetamide;
N-[(1R,2R,6S)-6-amino-2-(1-ethylpropoxy)-4-(thiophene-2-carbonyl)-3-cyclohexen-1-yl]acetamide hydrochloride;
N-[(1R,2R,6S)-6-amino-2-(1-ethylpropoxy)-4-(5-methylfuran-2-carbonyl)-3-cyclohexen-1-yl]acetamide;
N-[(1R,2R,6S)-6-amino-2-(1-ethylpropoxy)-4-(5-methylthiophene-2-carbonyl)-3-cyclohexen-1-yl]acetamide;
N-[(1R,2R,6S)-6-amino-2-(1-ethylpropoxy)-4-(4-fluorobenzoyl)-3-cyclohexen-1-yl]acetamide;
N-[(1R,2R,6S)-6-amino-4-benzoyl-2-(1-ethylpropoxy)-3-cyclohexen-1-yl]acetamide hydrochloride;
N-[(1R,2R,6S)-6-amino-2-(1-ethylpropoxy)-4-phenylacetyl-3-cyclohexen-1-yl]acetamide;
N—R[(1R,2R,6S)-6-amino-2-(1-ethylpropoxy)-4-(furan-2-carbonyl)-3-cyclohexen-1-yl]acetamide;
N-[(1R,2R,6S)-6-amino-2-(1-ethylpropoxy)-4-(1-methyl-1H-pyrrole-2-carbonyl)-3-cyclohexen-1-yl]acetamide;
N-[(1R,2R,6S)-6-amino-4-(2,2-dimethylpropionyl)-2-(1-ethylpropoxy)-3-cyclohexen-1-yl]acetamide;
N-[(1R,2R,6S)-6-amino-2-(1-ethylpropoxy)-4-(thiazole-2-carbonyl)-3-cyclohexen-1yl]acetamide;
N-[(1R,2R,6S)-6-amino-2-(1-ethylpropoxy)-4-pentanoyl-3-cyclohexen-1-yl]acetamide hydrochloride;
N-[(1R,2R,6S)-6-amino-4-benzoyl-2-(1-ethylpropoxy)-3-cyclohexen-1-yl]-2,2-dimethylpropionamide;
N-[(1S,5R,6R)-6-amino-3-benzoyl-5-(1-ethylpropoxy)-3-cyclohexen-1-yl]acetamide;
N-[(1S,5R,6R)-6-amino-5-(1-ethylpropoxy)-3-(thiophene-2-carbonyl)-3-cyclohexen-1-yl]acetamide;
N-[(1R,2R,6S)-6-amino-2-(1-ethylpropoxy)-4-(thiophene-2-carbonyl)-3-cyclohexen-1-yl]-3-methylbutylamide;
[(1R,2R,6S)-6-amino-2-(1-ethylpropoxy)-4-(thiophene-2-carbonyl)cyclohexen-3-yl]-3-ethylurea;
N-[(1R,2R,6S)-6-amino-2-(1-ethylpropoxy)-4-heptanoyl-3-cyclohexen-1-yl]acetamide;

N-[(1R,2R,6S)-6-amino-2-(1-ethylpropoxy)-4-(thiophene-3-carbonyl)-3-cyclohexen-1-yl]acetamide;

N-[(1R,2R,6S)-6-amino-4-cyclohexanecarbonyl-2-(1-ethylpropoxy)-3-cyclohexen-1-yl]acetamide hydrochloride; and N-[(1R,2R,6S)-6-amino-2-(1-ethylpropoxy)-4-(5-methoxythiophene-2-carbonyl)-3-cyclohexen-1-yl]acetamide hydrochloride.

7. A pharmaceutical composition comprising:

the compound according to claim 1, a pharmaceutically acceptable salt thereof, or a solvate thereof; and a pharmaceutically acceptable carrier.

8. A method for treating arrhythmia, comprising administering an effective amount of the compound according to claim 1, a pharmaceutically acceptable salt thereof, or a solvate thereof to a patient in need thereof.

* * * * *